United States Patent
Eck et al.

(10) Patent No.: US 7,393,436 B2
(45) Date of Patent: Jul. 1, 2008

(54) THERMAL SEPARATING PROCESS FOR REMOVING AT LEAST ONE STREAM CONTAINING ENRICHED (METH) ACRYLIC MONOMERS

(75) Inventors: Bernd Eck, Viernheim (DE); Ulrich Hammon, Mannheim (DE); Klaus Joachim Mueller-Engel, Stutensee (DE); Juergen Schroeder, Ludwigshafen (DE); Joachim Thiel, Neustadt (DE); Hans Martan, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 324 days.

(21) Appl. No.: 10/888,933

(22) Filed: Jul. 12, 2004

(65) Prior Publication Data
US 2005/0090628 A1    Apr. 28, 2005

Related U.S. Application Data

(60) Provisional application No. 60/487,587, filed on Jul. 17, 2003, provisional application No. 60/486,168, filed on Jul. 11, 2003.

(30) Foreign Application Priority Data

Jul. 11, 2003  (DE) .................... 103 31 720
Jul. 17, 2003  (DE) .................... 103 32 758

(51) Int. Cl.
*B01D 3/14* (2006.01)
*B01D 3/42* (2006.01)
*C07C 51/43* (2006.01)

(52) U.S. Cl. .............. 203/1; 203/2; 203/3; 203/87; 203/98; 203/DIG. 21; 261/151; 261/152; 526/51; 526/67; 562/600

(58) Field of Classification Search .............. 203/1–3, 203/87, 98, 100, DIG. 21; 526/61, 67; 261/151–152; 562/600
See application file for complete search history.

(56) References Cited

U.S. PATENT DOCUMENTS

| | | | | |
|---|---|---|---|---|
| 5,264,625 A | * | 11/1993 | Hammon et al. | 562/532 |
| 6,252,110 B1 | * | 6/2001 | Uemura et al. | 562/598 |
| 6,666,956 B1 | * | 12/2003 | Nishimura et al. | 203/1 |
| 6,676,808 B2 | * | 1/2004 | Hamamoto et al. | 203/8 |

FOREIGN PATENT DOCUMENTS

| | | |
|---|---|---|
| DE | A 195 36 191 | 4/1994 |
| DE | 43 08 087 | 9/1994 |
| DE | A 196 06 877 | 8/1997 |
| DE | A 198 51 984 | 5/2000 |
| DE | 199 24 533 | 11/2000 |
| DE | A 199 22 722 | 11/2000 |
| DE | A 199 24 532 | 11/2000 |
| DE | A 101 15 277 | 6/2002 |
| DE | A 101 56 016 | 6/2003 |
| DE | A 102 18 419 | 6/2003 |

(Continued)

*Primary Examiner*—Virginia Manoharan
(74) *Attorney, Agent, or Firm*—Oblon, Spivak, McClelland, Maier & Neustadt, P.C.

(57) ABSTRACT

A thermal separating process for removing a stream containing enriched (meth)acrylic monomers from a mixture containing (meth)acrylic monomers, in which the liquid phases retained in the separating space at high temperature and high (meth)acrylic monomer content are minimized.

13 Claims, 9 Drawing Sheets

FOREIGN PATENT DOCUMENTS

| | | |
|---|---|---|
| DE | A 102 51 328 | 6/2003 |
| DE | A 102 24 341 | 7/2003 |
| DE | 102 56 147 | 12/2003 |
| DE | A 102 23 058 | 12/2003 |
| DE | A 102 43 625 | 4/2004 |
| DE | A 102 47 240 | 4/2004 |
| EP | 270 999 | 6/1988 |
| EP | A 551 111 | 7/1993 |
| EP | 648 732 | 4/1995 |
| EP | A 695 736 | 2/1996 |
| EP | A 717 019 | 6/1996 |
| EP | A 0 733 617 | 9/1996 |
| EP | A 0 765 861 | 4/1997 |
| EP | 0 779 268 | 6/1997 |
| EP | 780 359 | 6/1997 |
| EP | 780 360 | 6/1997 |
| EP | A 778 255 | 6/1997 |
| EP | A 0 861 820 | 9/1998 |
| EP | A 0 982 287 | 3/2000 |
| EP | A 982 289 | 3/2000 |
| EP | A 990 636 | 4/2000 |
| EP | 1 026 145 | 8/2000 |
| EP | 1 110 940 | 6/2001 |
| EP | A 1 125 912 | 8/2001 |
| WO | WO 97/48669 | 12/1997 |
| WO | WO 98/08798 | 3/1998 |
| WO | WO 03/047714 | 6/2003 |

\* cited by examiner

THERMAL SEPARATING PROCESS FOR REMOVING AT LEAST ONE STREAM CONTAINING ENRICHED (METH) ACRYLIC MONOMERS

The present invention relates to a thermal separating process for removing at least one stream containing enriched (meth)acrylic monomers from a mixture containing (meth)acrylic monomers, comprising the continuous steady-state operation of at least one thermal separating apparatus which comprises at least one separating space with or without separating internals, into which at least one stream containing (meth)acrylic monomers is conducted and out of which at least one stream containing (meth)acrylic monomers is conducted, with the proviso that the stream which is conducted overall into the separating space and is obtained in a theoretical sense by adding the individual streams conducted into the separating space contains X % by weight of constituents other than (meth)acrylic monomers, the stream which is conducted out of the separating space with the highest proportion by weight of (meth)acrylic monomers contains Y % by weight of constituents other than (meth)acrylic monomers, the X:Y ratio is $\geq 5$, the separating space, except at the stream inlet and at the stream outlet points, is bounded by a solid phase and comprises at least one circulation heat exchanger, and the total volume filled with liquid phase in the separating space is $\geq 1\ m^3$, and the temperature of the liquid phase, at least in places, is $\geq 80°\ C$.

Figure 1:
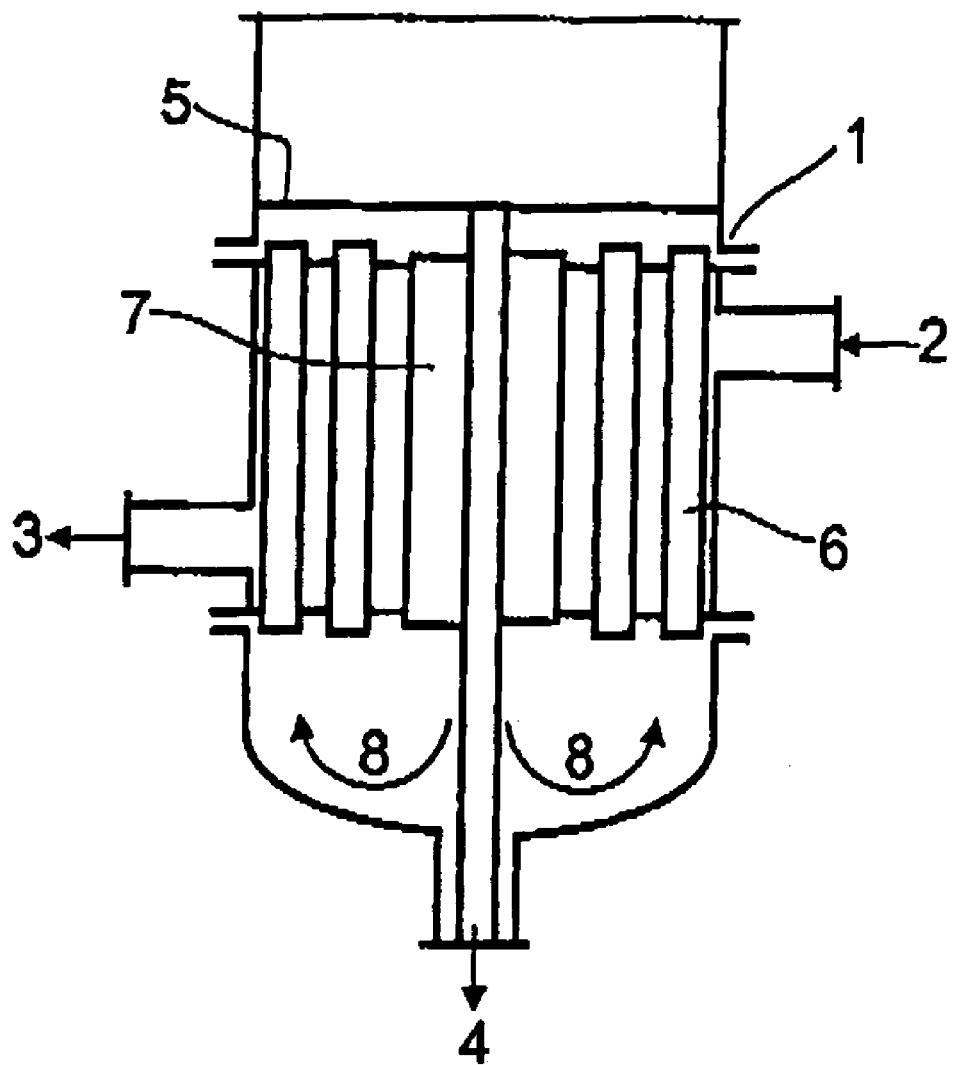
FIG. 1 shows a schematic diagram of a circulation evaporator.

In this document, the term steady-state operation means that the streams, with regard to their contents and flow rates, vary during the continuous operation in the particular unit selected by at most 5% (based on the mean value as the reference point). Preference is given in accordance with the invention to the aforementioned variance being $\leq 4\%$, more preferably $\leq 3\%$ and more preferably $\leq 2\%$ or $\leq 1\%$.

In this document the notation (meth)acrylic monomers is an abbreviation of "acrylic monomers and/or (meth)acrylic monomers".

In this document, the term acrylic monomers is an abbreviation of "acrolein, acrylic acid and/or esters of acrylic acid".

In this document, the term methacrylic monomers is an abbreviation of "methacrolein, methacrylic acid and/or esters of methacrylic acid".

In particular, the (meth)acrylic monomers addressed in this document are intended to include the following (meth)acrylic esters: hydroxyethyl acylate, hydroxyethyl methacrylate, hydroxypropyl acrylate, hydroxypropyl methacrylate, glycidyl acrylate, glycidyl methacrylate, methyl acrylate, methyl methacrylate, n-butyl acrylate, isobutyl acrylate, isobutyl methacrylate, n-butyl methacrylate, tert-butyl acrylate, tert-butyl methacrylate, ethyl acrylate, ethyl methacrylate, 2-ethylhexyl acrylate, 2-ethylhexyl methacrylate, N,N-dimethylaminoethyl methacrylate and N,N-dimethylaminoethyl acrylate.

(Meth)acrylic monomers are important starting compounds for preparing polymers which find use, for example, as adhesives.

(Meth)acrolein and (meth)acrylic acid are prepared on the industrial scale predominantly by catalytic gas phase oxidation of suitable $C_3/C_4$ precursor compounds (or of precursor compounds thereof), in particular of propene and propane in the case of acrolein and acrylic acid, or isobutene and isobutane in the case of methacrylic acid and of methacrolein.

However, suitable starting materials in addition to propene, propane, isobutene and isobutane are also other compounds containing 3 or 4 carbon atoms, such as isobutanol, n-propanol or precursor compounds thereof, for example the methyl ether of isobutanol. (Meth)acrylic acid can also be obtained from (meth)acrolein.

This normally results in a product gas mixture from which the (meth)acrylic acid or the (meth)acrolein has to be removed.

Esters of (meth)acrylic acid are obtainable, for example, by direct reaction of (meth)acrylic acid and/or (meth)acrolein with the corresponding alcohols. However, product mixtures are initially obtained in this case also, from which the (meth)acrylic esters have to be removed.

For the aforementioned removals, one or more thermal separating processes as described at the outset are frequently employed. These are customarily carried out continuously, by continuously feeding streams to and withdrawing streams from the separating space under steady-state conditions. It is characteristic of thermal separating processes that the separating action achieved by them requires the supply (for example for evaporation) and/or the removal (for example for condensing) of thermal energy, and that liquid phases are involved in them (are conducted in the separating space).

In general, this thermal energy is removed and/or supplied via circulation heat exchangers. A circulation heat exchanger is a portion of the separating space required in the process described at the outset, to which the liquid and/or gas phase withdrawn from another portion of the separating space is fed. In the circulation heat exchanger, thermal energy is supplied to and/or removed from this liquid and/or gas phase by a source which is not included in the separating space, in a direct (for example by the source being conducted into the space) and/or indirect manner. Subsequently, the cooled or heated liquid phase (may be partly and/or fully converted to the vapor phase in the heat exchange) and/or gas phase (may be partly and/or fully condensed in the heat exchange) is recycled fully into the other portion of the separating space, and the withdrawal point and the recycle point may be spatially separated. In many cases, the at least one circulation heat exchanger is a circulation evaporator.

The achievement of the thermal separating action itself (i.e. the performance of the thermal separating process) may in principle be achieved in separating spaces which include no separating internals, as is the case, for example, in a simple distillation. In this case, a liquid mixture is partially evaporated and the vapor phase which is generated and has a different composition to the liquid mixture is removed in vaporous and/or condensed form.

However, the thermal separating action is frequently achieved with the use of separating internals, and in many cases gaseous (usually ascending) and liquid (usually descending) streams are conducted in cocurrent or countercurrent. As a consequence of the inequilibrium existing between the streams, there is heat and mass transfer which ultimately results in the desired separation. In general, the separating internals are disposed in a separating column.

It is also characteristic of the thermal separating processes of this document that when the individual chemical compounds conducted through the separating space pass through the separating space, less than 20 mol % (based in each case on the total amount of the particular individual chemical compound conducted overall into the separating space) is chemically changed (excluding the Michael addition of the (meth)acrylic monomers; this is not to be counted as such a chemical change).

Frequently, the aforementioned percentage in the thermal separating processes of this document is at values of $\leq 10$ mol %, or $\leq 7$ mol % or $\leq 3$ mol % or $\leq 1$ mol %.

Examples of and therefore elements of the term "thermal separating process" used in this document are fractional condensation (cf., for example, DE-A 19 924 532) and/or rectification (ascending vapor phase is conducted in countercurrent to descending liquid phase: the separating action is based on the vapor composition at equilibrium being different to the liquid composition), absorption (at least one ascending gas is conducted in countercurrent to at least one descending liquid; the separating action is based on the different solubility of the gas constituents in the liquid), stripping (like absorption; however the liquid phase is laden with the component which is absorbed by the stripping gas) and desorption (the reverse process to absorption; the gas dissolved in the liquid phase is removed by partial pressure reduction). However, liquid/liquid extraction and crystallization (in particular falling-film and suspension crystallization) are also considered to be thermal separating processes in this document.

For example, the removal of (meth)acrylic acid or (meth)acrolein from the product gas mixture of the catalytic gas phase oxidation of propane and/or propene can be carried out in such a way that the (meth)acrylic acid or the (meth)acrolein is initially basically removed by absorption into a solvent (for example water or an organic solvent) or by fractional condensation of the product gas mixture, and the resulting condensate or absorbate is subsequently separated rectificatively (generally in a plurality of stages) to obtain more or less pure (meth)acrylic acid or (meth)acrolein (cf., for example, EP-A 717 019, EP-A 1 125 912, EP-A 982 289, EP-A 982287, DE-A 19 606 877, DE-A 1 011 527, DE-A 10 224 341, DE-A 10 218 419, DE-A 10 247 240 and DE-A 10 243 625).

The fractional condensation addressed above differs from the conventional rectification essentially in that the mixture to be separated is fed to the separating space in gaseous form (i.e. fully converted to the vapor form).

The gaseous and/or liquid mixtures which contain (meth)acrylic monomers and have already been addressed may contain the (meth)acrylic monomers either in more or less pure form or in dilution (for example with solvents or with diluent gases). The solvent may be either aqueous or an organic solvent, and the specific type of the organic solvent is essentially insignificant. The diluent gas may be, for example, nitrogen, carbon oxide ($CO$, $CO_2$), oxygen, hydrocarbon or a mixture of these gases.

This means that, for example on the route to obtaining (removing) (meth)acrylic monomers, thermal separating processes (as described at the outset) are applied in a highly differing manner to gaseous and/or liquid mixtures whose content of (meth)acrylic monomers may be $\geq 2\%$ by weight, or $\geq 10\%$ by weight, or $\geq 20\%$ by weight or $\geq 40\%$ by weight, or $\geq 60\%$ by weight, or $\geq 80\%$ by weight, or $\geq 90\%$ by weight, or $\geq 95\%$ by weight, or $\geq 99\%$ by weight (it will be appreciated that the content of (meth)acrylic monomers is always at values of <100% by weight). Frequently, the (meth)acrylic monomer content of such mixtures is from 10 to 40% by weight or from 90 to 99.5% by weight.

In general, these mixtures, in the process according to the invention itself, are conducted as a stream containing (meth)acrylic monomers into the at least one separating space.

Frequently, the separating space in the thermal separating processes described at the outset comprises a separating column. The (meth)acrylic monomers may accumulate either at the top or in the bottom of the separating column. However, it will be appreciated that fractions containing enriched (meth)acrylic monomers may also be withdrawn in the upper, lower or middle section of the separating column.

The separating internals used in the separating space, for example in the separating column, fulfill the purpose in thermal separating processes of increasing the surface area for the heat and mass transfer which brings about the separation.

Useful such internals are, for example, structured packings, random packings and or mass transfer trays.

The separating columns having separating internals for thermal separating processes are particularly frequently those which contain a sequence of mass transfer trays as at least a portion of the separating internals.

Mass transfer trays fulfill the purpose of providing locations having continuous liquid phases in the separating column in the form of liquid layers. The surface of the vapor or gas stream which, for example, ascends in the liquid layer and is thus distributed in the continuous liquid phase is then the decisive exchange surface. Mass transfer trays are preferably sealed to the wall surrounding them. A classic among the mass transfer trays is the sieve tray. In this document, this refers to plates whose passages for the ascending gas or vapor phase (the terms "gaseous" and "vaporous" are used synonymously in this document) are simple holes and/or slots.

The sieve trays are typically differentiated into two groups, i.e. into those having forced liquid flow and those without forced liquid flow.

Quite generally, forced liquid flow is achieved by the mass transfer trays having at least one downcorner (drain), through which the liquid, irrespective of the flow path of the vapor, flows from the upper tray to the lower tray (feed). The horizontal liquid flow over the transfer trays from feed to drain is selected in accordance with the process objective. The gas or the vapor passes through the open cross sections of the tray plate.

When the liquid is conducted over the tray in reverse flow (feed and drain of the mass transfer tray are disposed on the same side of the tray), these are referred to as reverse flow trays. In radial flow trays, the liquid flows radially on the tray from the middle (feed) to the drain at the edge of the tray.

In the crossflow trays, viewed over the entire flow area, the liquid is conducted transversely over the tray from feed to drain. In general, crossflow trays have a single-flow configuration. In other words, feed and drain are disposed on opposite sides of the tray. However, they may also have a double-flow (or else more than double-flow) configuration. In this case, the feed may be disposed, for example, in the middle and a drain on each of the opposite sides of the mass transfer tray.

In other words, the forced liquid flow in sieve trays is achieved by the sieve trays having, in addition to the passages for the ascending gas or vapor phase, at least one downcorner (drain), through which the liquid, irrespective of the flow path of the vapor, flows from the upper tray to the lower tray (feed). The liquid flows, for example, in transverse flow over the tray from at least one feed to at least one drain, in which case the feed pipe and drainpipe guarantee the liquid seal and the desired liquid height on the tray. Frequently (especially in the case of low column diameters), the sieve trays with forced liquid flow have a single-flow configuration. In other words, feed and drain are disposed on opposite sides of the tray. However, they may also have a double-flow (or else more than double-flow) configuration. In this case, the feed may be disposed, for example, in the middle and one drain on each of the opposite sides of the mass transfer tray. Such sieve trays are to be referred to hereinbelow as forced sieve trays. In these trays, trickle-through of the liquid which reduces the separating action is not, as in the case of hydraulically sealed crossflow trays, prevented by chimneys, into which the passages continue, but rather a minimum vapor loading is required for this purpose. The vapor ascends through the passages and bubbles through the liquid layer maintained by the drainpipe.

The dual-flow, or else trickle sieve, trays differ from the forced sieve trays in that they contain no drain segment. The absence of drain segments (downcorners) in the dual-flow trays results in the ascending gas and the liquid descending in the separating column passing through the same passages of the tray. As in the case of forced sieve trays, a minimum vapor loading is also required in the case of dual-flow trays, in order to achieve appropriate separating action. When the vapor loading is significantly lower, ascending gas and descending reflux move past each other substantially without exchange and the tray is at risk of running dry.

In other words, in the case of dual-flow trays too, a lower limiting rate has to be present so that a certain liquid layer is maintained on the tray, in order to allow the tray to work. In the normal working range, the liquid in dual-flow trays trickles through the passages from tray to tray, and the continuous gas phase between the trays is interspersed by a divided liquid phase.

Compared to sieve trays, It is characteristic of hydraulically sealed crossflow trays that they cannot run dry when the column is shut down, disregarding the tiny emptying drillhole (its cross section is normally more than 200 times smaller than the total cross section of the passages) which each crossflow tray has for reasons of utility.

In other words even at low column loadings, hydraulically sealed crossflow trays have accumulated liquid (reflux and/or feed liquid) and are at no risk of running dry. This results from the fact that the passages of hydraulically sealed crossflow trays are not chimneyless drillholes, as is the case in sieve trays. Rather, each passage opens into a chimney which prevents the tray from running dry. Above the chimney, vapor deflecting hoods (bubble-caps) are mounted which are immersed in the accumulated tray liquid. Frequently, the vapor deflecting hoods are slotted or serrated at their edges (i.e. they have transport slots). The vapor stream ascending through the passage is deflected by the vapor deflecting hoods and flows parallel to the tray, i.e. at right angles to the column, into the accumulated liquid.

The vapor bubbles leaving adjacent hoods which are generally distributed equidistantly over the tray form a froth layer in the accumulated liquid.

Drainpipes or drain segments which leave trays, generally to the left or right in alternation, supported by weirs, control the liquid level of the mass transfer trays and feed the liquid to the tray below. It is essential for the hydraulic sealing action that the drainpipes or drain segments of the upper tray are immersed in the accumulated liquid of the tray below. There are preferably no feed weirs. Bubble-caps which can be adjusted in height allow adaptation to the flow conditions and the equalization of the immersion depths in the event of production irregularities, so that all bubble-caps of the tray have uniform gas flow.

Depending on the design and arrangement of the bubble-caps, the hydraulically sealed crossflow trays having single-flow configuration are divided, for example, into round bubble-cap trays (passage, chimney and bubble-cap are round), tunnel-cap trays (passage, chimney and bubble-cap are rectangular, the bubble-caps are arranged in succession with the longer rectangular edge aligned parallel to the crossflow direction of the liquid) and Thormann trays (passage, chimney and bubble-cap are rectangular, the bubble-caps are arranged in succession with the longer rectangular edge at right angles to the crossflow direction of the liquid).

In this document, valve trays are crossflow trays which have tray drillholes having limited-stroke plate, ballast or lifting valves (floating flaps) which adapt the size of the vapor passage to the particular column loading. The ascending gas stream is deflected, flows parallel to the tray into the accumulated reflux liquid and forms a froth layer. Drainpipes equipped with weirs conduct the reflux from tray to tray. Frequently, they have double-flow configuration. However, they may also have triple-flow and multiflow (for example up to octuple-flow) configuration.

Mass transfer trays on which there is equilibrium between descending liquid and rising vapor are referred to as theoretical plates.

This term can be applied to all other separating internals which are suitable for countercurrent distillations (rectifications) (such as structured packings and random packings) and to other thermal separating procedures such as sorption and extraction. In the case of the latter too, the separating internals mentioned bring about an increase in the exchange surface between then two liquid phases.

It is therefore appropriate to refer generally to theoretical plates. A theoretical plate is defined as the spatial unit which brings about enrichment in accordance with the thermodynamic equilibrium.

The aim of a thermal separating process for removing at least one stream containing enriched (meth)acrylic monomers from a mixture containing (meth)acrylic monomers is firstly a very high degree of enrichment of the (meth)acrylic monomers in the removed stream containing enriched (meth)acrylic monomers and secondly a very high space-time yield of this removed stream.

A disadvantage of the thermal separating processes described at the outset is that those measures which, under otherwise constant boundary conditions, increase the degree of enrichment normally at the same time reduce the space-time yield (for example an increase in the number of theoretical plates typically improves the degree of enrichment; but an increase in the number of theoretical plates under otherwise identical boundary conditions normally decreases the space-time yield).

It is an object of the present invention to break through the aforementioned relationship and to provide a thermal separating process as described at the outset for removing at least one stream containing enriched (meth)acrylic monomers from a mixture containing (meth)acrylic monomers, in which the degree of enrichment and space-time yield are at the same time increased.

We have found that this object is achieved by a thermal separating process for removing at least one stream containing enriched (meth)acrylic monomers from a mixture containing (meth)acrylic monomers, comprising the continuous steady-state operation of at least one thermal separating apparatus which comprises at least one separating space with or without separating internals, into which at least one stream containing (meth)acrylic monomers is conducted and out of which at least one stream containing (meth)acrylic monomers is conducted, with the proviso that the stream which is conducted overall into the separating space and is obtained in a theoretical sense by adding the individual streams conducted into the separating space contains X % by weight of constituents other than (meth)acrylic monomers, the stream which is conducted out of the separating space with the highest proportion by weight of (meth)acrylic monomers contains Y % by weight of constituents other than (meth)acrylic monomers, the X:Y ratio is $\geq 5$, the separating space, except at the stream inlet and at the stream outlet points, is bounded by a solid phase and comprises at least one circulation heat exchanger, and the total volume filled with liquid phase in the separating space is $\geq 1$ m$^3$, and the temperature of the liquid phase is at least $\geq 80°$ C., wherein in the case that the separating space is divided into n individual volume elements and the highest and the lowest temperatures of the liquid phase disposed in an individual volume element do not differ by more than 2° C. and the volume element is continuous within the separating space, the overall residence time $t_{ort}$, $$t_{ort} = \sum_{i=1}^{n} \frac{m_{al}}{\dot{m}_l} \cdot 2^A,$$

is $\leq 20$ h, where
$A = (T_i - T_o)10°$ C.,
$T_o = 100°$ C., $T_i$ = the arithmetic mean of the highest and lowest temperature existing the liquid phase of the volume element i in ° C., $m_{si}$ = the total amount of (meth)acrylic monomers present in the volume of the liquid phase present in the volume element i, $\dot{m}_i$ = the total amount of liquid phase stream conducted out of the volume element i, and

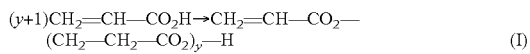

with the proviso that the sum over all volume elements i includes neither volume elements i having a liquid phase mass $m_i$ present therein and $m_i/\dot{m}_i \geq 100$ h, as deadspace volume elements, nor volume elements i which have no liquid phase, and the total amount of the liquid phase present in the deadspace volume elements is not more than 5% by weight of the overall liquid phase present in the separating space.

The background to the procedure according to the invention is the fact that methacrylic monomers form oligomers or polymers (Michael adducts) by simple or multiple Michael addition.

In the case of acrylic acid, these satisfy, for examples the general formula I $(y+1)CH_2=CH—CO_2H \rightarrow CH_2=CH—CO_2—$
$(CH_2—CH_2—CO_2)_y—H$ (I)

where y=in particular from 1 to 6, sometimes even >6.

The character of the Michael adduct formation is disclosed, inter alia, by EP-A 733 617, EP-A 765 861, DE-A 19 536 191, DE-A 19 851 984, DE-A 19 927 722, EP-A 780 360, EP-A 780 359, WO 98/08798, WO 97/48669 and DE-A 19 924 533.

A disadvantage of the Michael adduct formation of (meth)acrylic monomers is that they are also effected in the course of thermal separating processes for removing a stream containing enriched (meth)acrylic monomers from a mixture containing (meth)acrylic monomers, thus reducing both the degree of enrichment and the space-time yield. The prior art regards merely the isolation and subsequent dissociation of the Michael adducts as a possible solution to the problem (cf., for example, EP-A 780 359, EP-A 780 360, WO 98/08798 and DE-A 19 924 533).

Detailed investigations have led to the process according to the Invention as a further contribution to the solution to the problem.

This contribution to the solution to the problem takes into account that a Michael adduct of (meth)acrylic monomers is formed substantially only in the liquid phase. It is also taken into account that the rapidity of Michael adduct formation in the liquid phase increases both with increasing temperature and with increasing proportion by mass of the (meth)acrylic monomers in the liquid phase, a temperature increase of 10° C. resulting approximately in a doubling of the reaction rate. Distinctly below 100°C. the Michael addition of acrylic monomers is substantially negligible.

In other words, when care is taken in continuously operated thermal separating processes for removing at least one stream containing enriched (meth)acrylic monomers from a mixture containing (meth)acrylic monomers in steady-state operation that the residence time of the (meth)acrylic monomers in the liquid phase is particularly low where temperature and proportion by mass of (meth)acrylic monomers in the liquid phase are high, the disadvantageous Michael adduct formation of (meth)acrylic monomers in the course of such thermal separating processes can be prevented to a certain extent.

A suitable measure in this regard is a mean overall residence time of the (meth)acrylic monomers which they have in the liquid phase in the separating space in the thermal separating process and is calculated in an appropriate manner from individual residence times.

To this end, the separating space is divided into n individual volume elements. The size and number n of these volume elements is substantially insignificant in other words, the individual volume elements may either be of equal size or have different volumes. It is essential only that the highest and the lowest temperatures of the liquid phase in an individual volume element do not differ by more than 2° C. and that the volume element is continuous within the separating space (as will be seen, the temperature requirement takes into account the temperature dependence of the Michael addition).

The individual residence time $t_i$ of the (meth)acrylic monomers in the volume element i is then given by $t_i = m_i/\dot{m}_i$, $m_i$ is the total mass of liquid phase present in the volume element i and $\dot{m}_i$ is the total mass flow rate of liquid phase conducted out of the volume element i (in the steady state, this is equal to the total mass flow rate of liquid phase fed to the volume element i).

This individual residence time is multiplied by the quotient $m_{si}/m_i$ in order to take into account the proportion by mass of the (meth)acrylic monomers in the volume element i.

The factor $2^A$ where $A=(T_i-T_o)/10°$ C. weights the individual residence time additionally and takes into account the temperature in the liquid phase of the volume element i. Finally, it is necessary to sum over all volume elements i which contain liquid phase.

Deadspace volume elements i are not to be included in the sum in that they are substantially not involved in the separating process. This is especially true when their $m_i/\dot{m}_i$ is $\geq 200$ h, or $\geq 300$ h, or $\geq 400$ h, or $\geq 500$ h, or $\geq 750$ h, or $\geq 1000$ h.

Deadspace volume elements essentially take no part in the exchange processes which bring about the separating action in the separating process according to the invention. These volume elements are substantially isolated volume elements which fill once with liquid phase and contain substantially one and the same liquid phase over the time.

In principle, deadspace volume elements are to be very substantially avoided in the process according to the invention, especially because they have an increased probability of the commencement of free-radical polymerization of the (meth)acrylic monomers present therein.

In other words, the process according to the invention is advantageous especially when the total amount of liquid phase present in the deadspace volume elements is not more than 4% by weight, preferably not more than 3% by weight more preferably not more than 2% by weight and most preferably not more than 1% by weight or is even insignificant.

It is also essential for the process according to the invention that X:Y $\geq 5$. In other words, the number of theoretical plates is not impaired by the process according to the invention. Rather, the individual residence time $t_i$ will be reduced in the process according to the invention in particular when firstly $m_{si}/m_i$ and A are large and a reduction of $t_i$ substantially does not impair the number of theoretical plates.

The process according to the invention can thus also be employed when X:Y $\geq 8$, or $\geq 10$, or $\geq 15$, or $\geq 20$, or $\geq 30$, or $\geq 40$, or $\geq 50$.

In general, X:Y in the process according to the invention will not exceed 200. Usually, X:Y in the process according to the invention will be $\leq 175$, in many cases $\leq 150$ or $\leq 100$.

The procedure according to the invention is advantageous in particular when the total volume V filled with liquid phase in the separating space has a large volume. In other words, V in the process according to the invention may be $\geq 2$ m³, or $\geq 4$ m³, $\geq 5$ m³, or $\geq 7$ m³, or $\geq 9$ m³, $\geq 10$ m³, or $\geq 15$ m³. In general, V will not be more than 500 m³. In other words, V in the process according to the invention will generally be $\leq 450$ m³, frequently $\leq 400$ m³, often $\leq 350$ m³ and usually $\leq 300$ m³.

As a consequence of the high boiling point of (meth)acrylic monomers, the temperature of the liquid phase in the separating space in the process according to the invention will frequently, at least in places, be $\geq 90°$ C., or $\geq 100°$ C., or $\geq 110°$ C., or $\geq 120°$ C., or $\geq 130°$ C., or $\geq 140°$ C., or $\geq 150°$ C., or $\geq 160°$ C., or $\geq 170°$ C., or $\geq 180°$ C. However, the highest temperature of the liquid phase in one volume element i in the process according to the invention will generally not exceed 250° C. Normally, this highest temperature will be $\leq 230°$ C., frequently $\leq 210°$ C. and in many cases $\leq 200°$ C. These temperatures are generally not capable of achieving significant dissociative action, since this requires that the dissociation products are continuously removed from the dissociation equilibrium.

Advantageously, the overall residence time $t_{ort}$ in the process according to the invention is $\leq 15$ h, or $\leq 10$ h. Particularly advantageously in accordance with the invention, $t_{ort}$ is $\leq 8$ h, or $\leq 6$ h or $\leq 4$ h, or $\leq 2$ h. However, $t_{ort}$ in the process according to the invention will generally be $\geq 0.5$ h or $\geq 1$ h.

The process according to the invention is suitable, inter alia, to the rectificative processes described in the documents EP-A 648 732 and EP-A 270 999 for purifying crude (meth) acrylic acid, to the processes for fractional condensation described in the documents DE-A 19 924 533. DE-A 10 247 240 and DE-A 10 243 625 for basically removing crude acrylic acid from the product gas mixture of a propane and/or propane partial oxidation to acrylic acid, to the process described in EP-A 717 029 for rectificative removal of crude (meth)acrylic acid from a mixture comprising (meth)acrylic acid and an inert hydrophobic organic liquid having a higher boiling point than (meth)acrylic acid as a main constituent, to the absorptive removal described in DE-A 4 308 087 of acrylic acid from the reaction gases of the catalytic partial oxidation of propane and/or acrolein, and also to other rectificative, sorptive and/or extractive thermal separating processes for removing at least one stream containing enriched (meth)acrylic monomers from a mixture containing (meth)acrylic monomers which are described in these documents and also in EP-A 990 636, EP-A 861 820, EP-A 778 255, EP-A 551 111, EP-A 695 736, EP-A 1026145 and DE-A 10 251 328 and/or cited by reference literature.

Usually, the separating space in the aforementioned processes and in the process according to the invention quite generally includes at least one circulation heat exchanger and at least one column with or without separating internals.

Since absorptive removals generally proceed exothermically, the at least one circulation heat exchanger in this connection generally fulfills the purpose of heat removal. This is normally effected by an indirect route by means of a cold carrier (coolant) which never enters the separating space. In other words, only one of the two spatial sides of the indirect heat exchanger is a constituent of the separating space. The other is outside and conducts the cold carrier, The streams are conveyed through the spatial side of the heat exchanger belonging to the separating space typically by means of at least one pump.

In the majority of the thermal removals which differ from absorptive removal, heat is supplied to the separating space via the circulation heat exchanger. In most cases, this is likewise effected by an indirect route by means of a heat carrier which never enters the separating space. In other words, only one of the two spatial sides of the indirect heat exchanger is a constituent of the separating space. The other is outside and conducts the heat carrier. Frequently, sufficient heat is supplied that boiling phenomena occur in the spatial side of the heat exchanger belonging to the separating space.

In this case, the circulation heat exchanger is referred to as a circulation evaporator. The stream can be conveyed through the spatial side of the heat exchanger belonging to the separating space by means of a pump (forced circulation) and/or by natural circulation (the latter proceeds as a consequence of the difference in the mass density between heated and unheated stream).

Especially when the thermal separating process according to the invention is a rectification, the circulation heat exchanger used is a circulation evaporator.

In principle, the indirect circulation heat exchangers used in the process according to the invention may be all known indirect heat exchanger types. Preference is given to selecting them in such a way that the liquid phase volume retained therein is minimal.

Useful circulation evaporators are, for example, Robert evaporators (natural circulation evaporators) integrated into the separating column as outlined in FIG. 1 (1=separating column, 2=heating vapor, 3=heating vapor condensate, 4=bottom effluent, 5=liquid level, 6=evaporator tube, 7=central falling tube, 8=circulation direction).

Figure 2:
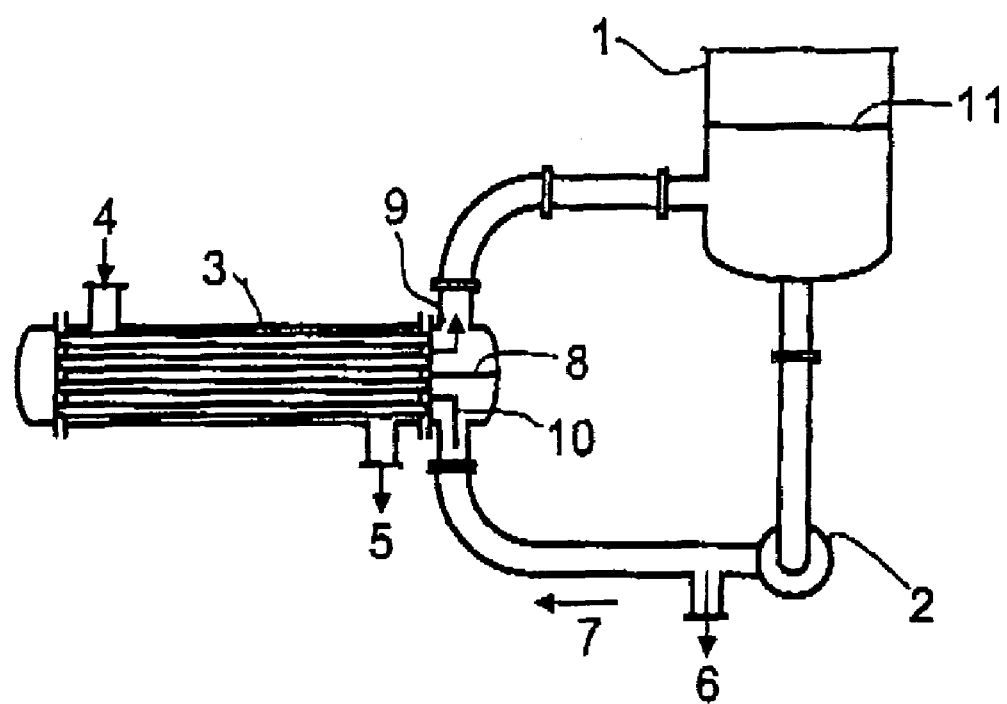
FIG. 2 shows a schematic diagram where the circulation evaporator may also be a forced circulation evaporator installed outside the separating column.

However, the circulation evaporator may also be a forced circulation evaporator installed outside the separating column as shown by FIG. 2 (1=separating column, 2=circulation pump, 3=tube evaporator, 4=heating vapor, 5=heating vapor condensate, 6=bottom product withdrawal, 7=circulation direction, 8=separating apparatus, 9=outlet, 10=inlet, 11=liquid level).

Figure 3:
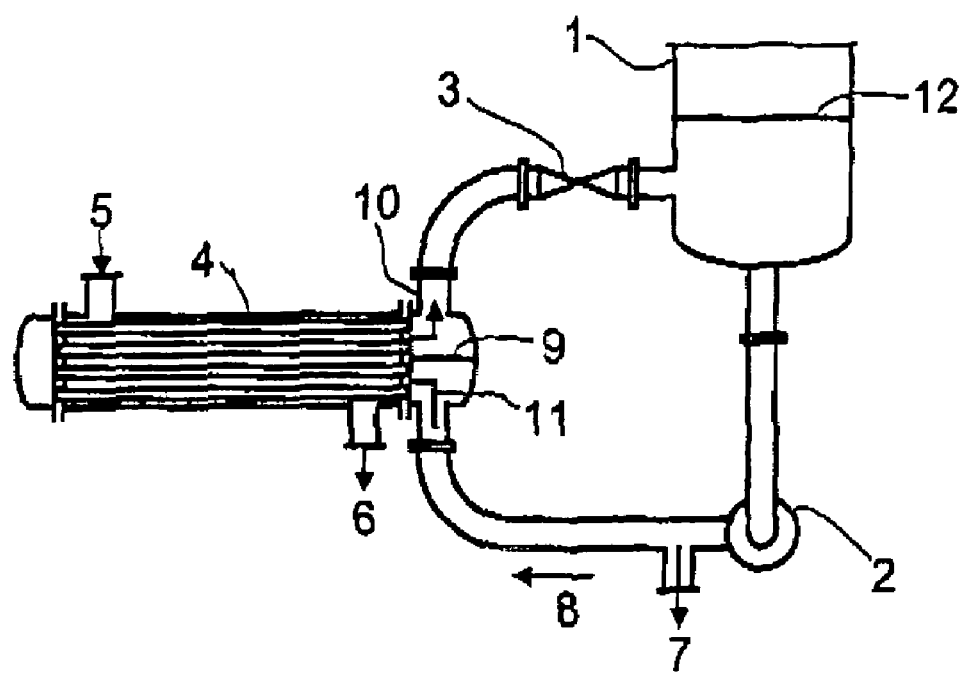
FIG. 3 shows a schematic diagram where the circulation evaporator used may also be a forced circulation flash evaporator.

It will be appreciated that the circulation evaporator used may also be a forced circulation flash evaporator, as shown schematically by FIG. 3 (1=separating column, 2=circulation pump, 3=throttle apparatus, 4=tube evaporator, 5=heating vapor, 6=heating vapor condensate, 7=bottom product withdrawal, 8=circulation direction, 9=separating apparatus, 10=outlet, 11=inlet, 12=liquid level). In contrast to the forced circulation evaporator, the forced circulation flash evaporator is separated from the separating column by a throttle apparatus. A portion of the liquid contents of the separating column at a pressure $P_x$ is continuously withdrawn and pumped into the feeds of, for example, a tube evaporator (tube bundle heat exchanger) by means of a circulation pump. Around the internal tubes of the tube evaporator flows a heat carrier, for example heating vapor (generally steam under pressure) whose temperature is above the temperature of the liquid contents of the separating column. On the path through the inlet and outlet tubes of the tube evaporator, the separating column liquid withdrawn is heated by indirect heat exchange to a temperature $T_y$, which is above the temperature of the liquid contents of the separating column.

A throttle apparatus separates tube evaporator and separating column on the pressure side and, by suitable choice of the circulation pump output, allows a throttle pressure $P_y$ to be set which is above $P_x$ and is above the boiling pressure $P_y$, corresponding to the temperature $T_y$, of the separating column liquid withdrawn. The above measures suppress boiling of the portion of separating column liquid pumped by circulation in the tubes of the tube evaporator. The proportion of the separating column liquid pumped by circulation is actually superheated in the tubes of the tube evaporator with respect to the pressure $P_x$ above the liquid contents of the separating column and the boiling process is thus shifted to the passage side of the throttle apparatus (i.e. the contents of the tubes of the tube evaporator are in monophasic form and the tube evaporator functions merely as a superheater). The passage of the superheated liquid through the throttle apparatus into the separating column may then be directly into the liquid contents of the separating column (the separating column bottoms). Under these conditions, the temperature of the liquid contents of the separating column bottoms regularly corresponds to the boiling temperature $T_x$ corresponding to the pressure $P_x$ above the bottoms liquid.

However, the superheated liquid may in principle also pass through the throttle apparatus into the separating column above the liquid level of the separating column bottoms. Under these conditions, the temperature of the liquid contents of the separating column bottoms is regularly below the boiling temperature $T_x$ corresponding to the pressure $P_x$ above the bottoms liquid. It is essential that the evaporative action of the tube evaporator installed outside the separating column does not occur until within the separating column, i.e. outside the circulation evaporator. The throttle may be, for example, mechanical (perforated plates, valves) and/or hydrostatic (by a bottoms liquid column of appropriate height via the passage of the superheated liquid).

Figure 4:
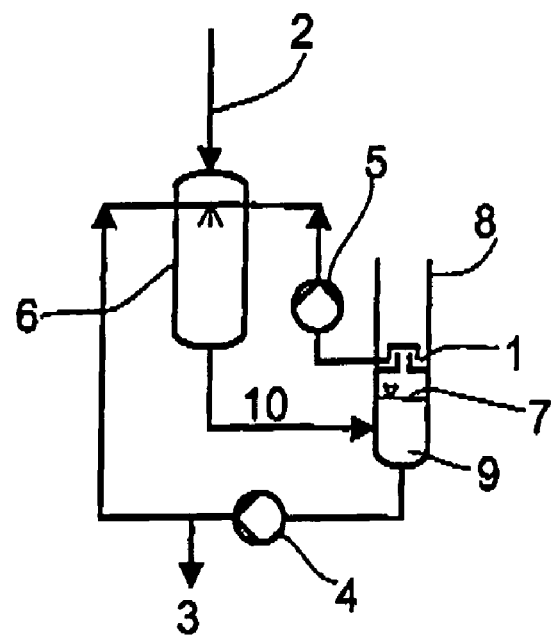
FIG. 4 shows a schematic diagram where the circulation evaporator may also be a direct circulation evaporator.

However, the circulation evaporator may also be a direct circulation evaporator, as shown by way of example in FIG. 4, into which the heat carrier generated outside the separating space is conducted and directly contacted with the liquid to be evaporated.

Bottoms liquid is withdrawn from the bottom 9 of the separating column 8 and/or high boiler fraction is withdrawn from a collecting tray 1 disposed in the lower section of the separating column. Either one or both liquid withdrawals are then sprayed into the direct circulation evaporator 6, in which, for example, they are conducted in cocurrent with the product gas mixture 2 having a higher temperature of a propene and/or propane partial oxidation as the direct heat carrier, and brought into direct heat exchange with it and thus at least partly evaporated. Subsequently, the entire mixture 10 is recycled into the bottoms liquid (recycling does not have to be immersed) of the separating column and the gas mixture which ascends therefrom is fractionally condensed ascending into itself.

Figure 5:
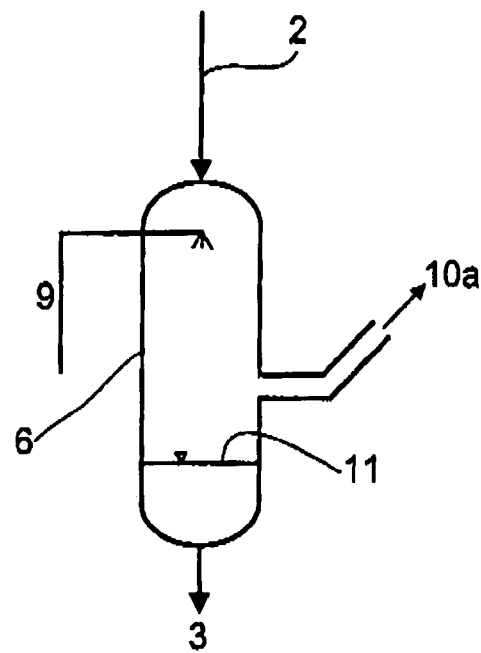
FIG. 5 shows a schematic diagram where the gas and liquid phase from the direct circulation evaporator may also be recycled spatially separated into the separating column.

The liquids withdrawn from the separating column are conveyed by means of pumps 4, 5, 3 is the bottom product withdrawal and 7 is the level of the bottoms liquid. The direct circulation evaporator is generally free of separating internals and is of cylindrical geometry. In principle, the gas and liquid phase from the direct circulation evaporator may also be recycled spatially separated into the separating column. Such a direct circulation evaporator is shown schematically by FIG. 5. The numbers have the same definition as in FIG. 4.

10a is the gas phase recycled into the separating column and 10b is the liquid phase recycled into the separating column. 11 is the liquid level in the direct circulation evaporator.

The separating column may either be free of separating internals, or contain separating internals, in which case useful separating internals for carrying out the process according to the invention are in principle all separating internals already mentioned in this document themselves or optionally together with other separating internals.

Useful bed-type packings are, for example, Raschig glass rings, saddles, wire mesh rings, V2A spirals, Pall rings and Stedman bodies, and also random packings of the second, third and fourth generation.

Useful insert-type packings whose diameter is substantially equal to the column internal diameter are structured packings of highly differing types. These are generally porous, large-surface area, three-dimensional metal, plastics and/or ceramics networks.

When the thermal separating process according to the invention is a fractional condensation of the gas mixture of a one- or two-stage heterogeneously catalyzed partial oxidation of propene and/or propane to acrylic acid, the separating column is preferably one whose separating internals, from bottom to top, are initially dual-flow trays and then hydraulically sealed crossflow trays (for example Thormann® trays or modified Thormann trays), as recommended by DE-A 19924532, DE-A 10243625 and DE-A 10 247 240.

The number of theoretical plates is appropriately from 15 to 30 and preferably 20. The evaporator is appropriately a direct circulation evaporator as described above. When an acid water quench is also integrated into the condensation column, useful separating internals for this region of the condensation column are preferably valve trays, as described by DE-A 19924532, DE-A 10243625 and DE-A 10 247 240.

In the general formula for $t_{ort}$, $t_{ort}$ in the process according to the invention is small when $m_{si}$ is very small while $\dot{m}_i$ is at the same time large. In other words, the inventive aim can be achieved, inter alia, by, with substantially equal streams and theoretical plates, minimizing the total amount of liquid phase retained in the separating space in the steady state, and in particular in those volume elements in which the liquid phase has a particularly high temperature and whose minimization does not reduce the number of theoretical plates. Among others, the possibilities which follow are available. A first possibility is to reduce the tubular cross sections of the pipe lines of the separating space through which liquid phase containing (meth)acrylic monomers is conducted at the cost of a certain pressure drop (at the same volume flow rate) and minimize the tube length.

In a fractional condensation to be carried out as described, it is advantageous in the context of the present invention when, apart from a direct circulation evaporator, no further circulation heat exchanger belongs to the separating space.

In other words, unlike the recommendation of FIG. 1 and FIG. 2 of DE-A 19924533 or in the FIG. of DE-A 19924532 and unlike the recommendation of DE-A 10 247 240, the circulation heat exchanger 8 of the aforementioned figures would preferably be completely dispensed with in accordance with the invention and the heat of evaporation would be drawn exclusively from the product gas mixture of the partial oxidation (of, for example, propene and/or propane to acrylic acid). According to the invention, a direct circulation evaporator will preferably not be configured as in FIG. 5 but rather as in FIG. 4, in which the mixture of gas and liquid is conducted into the separating column directly as a biphasic system, which, in contrast to the process control of FIG. 5, prevents the formation of additional liquid level (with increased individual residence time). At the same time, the cross section of the direct circulation evaporator at the same circulation rate (the direct circulation evaporator functions at the same time as a direct cooler for the product gas mixture of the partial oxidation; for reasons relating to heat balance, a certain minimum circulation rate is required) will be kept at a minimum, in order thus to keep to a minimum the total amount of liquid phase retained in the system of the separating space.

When the separating internals of the separating space are mass transfer trays, these mass transfer trays will in accordance with the invention advantageously be sieve trays, more preferably trickle sieve trays (dual-flow trays). Since the latter have no overflow weirs, they can be operated with a particularly low liquid level and are preferred in accordance with the invention over hydraulically sealed crossflow trays. The latter will be used only when the separating action achievable with dual-flow trays is not adequate.

When the separating space includes collecting trays (for example as a constituent of the separating column), from which, for example, liquid stream removed can be conducted out of the separating space (for example into the storage tank or into the circulation heat exchanger), it will be operated in accordance with the invention with a very low liquid level. This is made possible, for example, by applying displacement bodies to the collecting trays. These allow an increased liquid level at reduced liquid volume. An alternative solution is offered by DE-A 10159825 in the form of collecting trays having slopes.

It has been found that appropriate displacement bodies are generally also advantageous in the process according to the invention in the bottom segments (bottom spaces) of the separating columns. These are generally those spatial fractions which, in a geometric sense, are below the lowermost separating internals. In particular in the case of a rectification as the separating process according to the invention, bottoms liquid is regularly removed from the bottom segments, in order to feed it, for example, to forced circulation heat exchangers. At the same time, the bottoms liquid is generally in a state of boiling.

In order to prevent the pump required for forced circulation in the forced circulation heat exchanger from drawing too much gas, for example in the event of operating faults (this generally reduces the conveying output of the pump and in unfavorable cases can lead to its destruction, since the pump is normally configured only to convey liquid), a safety liquid head, a safety liquid level, is typically established in the bottom segment.

Figure 6:
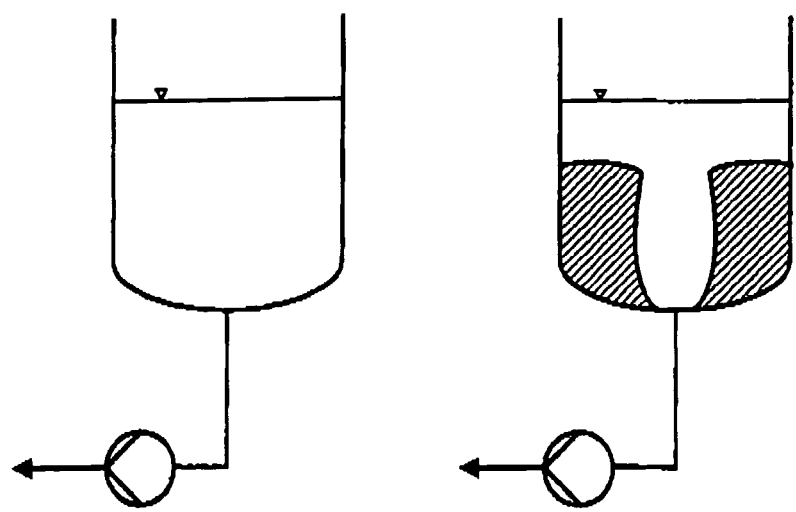
FIG. 6 shows a schematic diagram where displacement bodies can be introduced in the bottom space or contracting the bottom space.

This safety head is advantageously achievable in accordance with the invention with reduced bottom volume by introducing displacement bodies in the bottom space or contracting the bottom space, as shown, for example, by FIG. 6. It will be appreciated that this reduction of the bottom volume in the process according to the invention can be applied quite generally.

Figure 7:
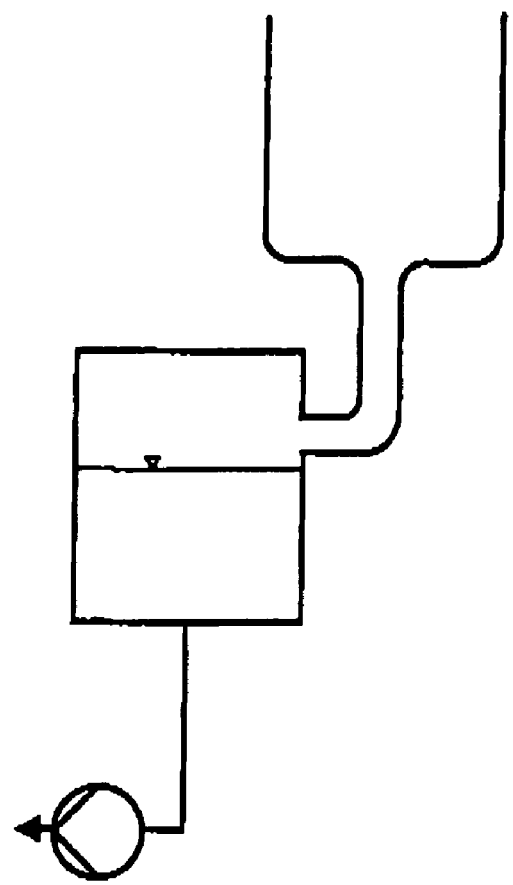
FIG. 7 shows a schematic diagram where a bottoms liquid buffer vessel is connected between pump and column bottom for safety reasons.

It is to be preferred in accordance with the invention in any case over those solutions as shown by FIG. 7 where a bottoms liquid buffer vessel is connected between pump and column bottom for safety reasons. Pumps used in accordance with the invention are appropriately selected in such a way that they retain a very small amount of liquid.

The determination of the temperatures $T_i$ in the process according to the invention is possible in a simple manner by experimental determination (for example by means of thermoelements mounted in a suitable manner).

In principle, the selection of the volume elements i in the process according to the invention is arbitrary and has substantially no effect on the result of $t_{ort}$. However, there is in many cases a particularly appropriate selection of the volume elements i.

Figure 8:
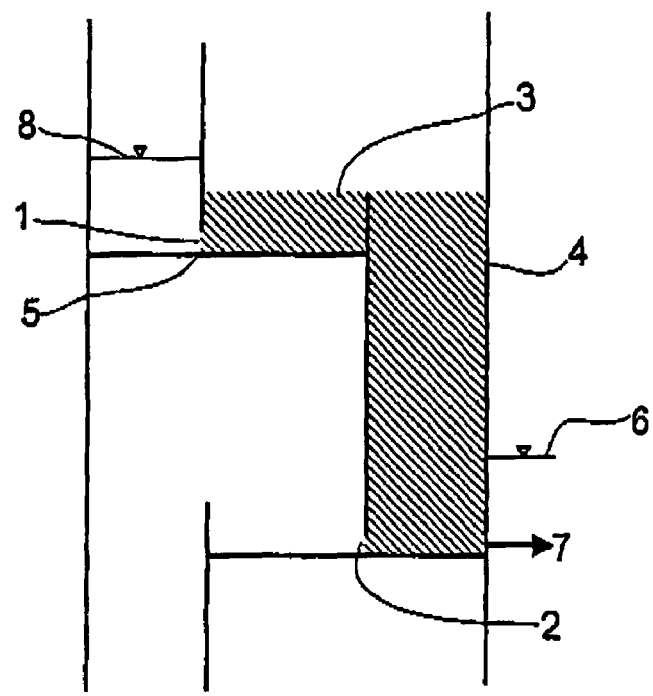
FIG. 8 shows a schematic diagram where mass transfer trays with forced flow, the volume elements is appropriately that volume element which includes the liquid level on the mass transfer tray and the feed to the mass transfer tray below

In the case of mass transfer trays with forced flow, the volume element i selected is appropriately that volume element which includes the liquid level on the mass transfer tray and the feed to the mass transfer tray below, as shown schematically in FIG. 8 by the hatched area. 1 is the inlet point to the volume element, 2 is the outlet point from the volume element, 3 is the overflow weir, 4 is the column wall and 5 is the mass transfer tray having the passages (6=liquid level in the downcorner or upcorner).

Figure 9:
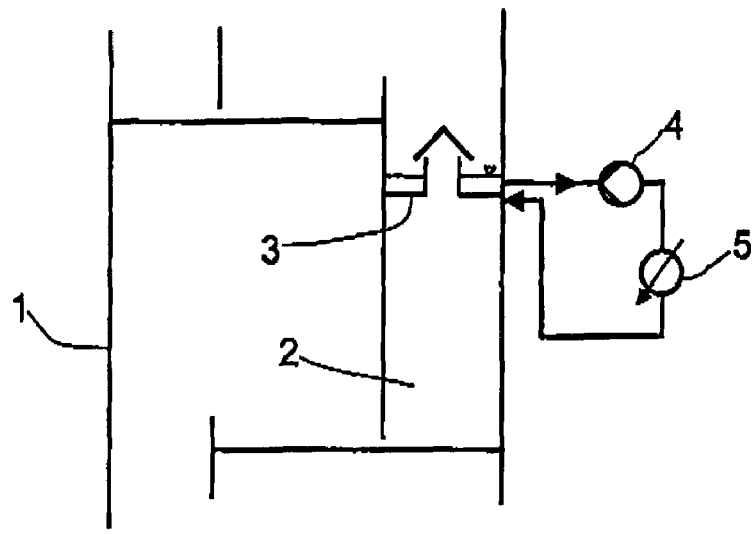
FIG. 9 shows a schematic diagram where installing a collecting tray in the downcorner, determining the liquid flow rate conducted out of the separating column and fed to it and recycling it into the downcorner below the output point

$m_{si}$ can be determined, for example, by simultaneously closing inlet and outlet point in the course of operation and subsequently determining the mass of liquid phase $m_i$ present in the volume element i. By means of chemical content analysis, $m_i$ finally results in $m_{si}$. $\dot{m}_i$ can be determined, for example, by installing a collecting tray in the downcorner, determining the liquid flow rate conducted out of the separating column and fed to it and recycling it into the downcorner below the output point (outlet point) (cf. FIG. 9; 1=column wall; 2=downcorner, 3=collecting tray, 4=conveying pump; 5=flow meter). Alternatively, $\dot{m}_i$ can also be determined for a given $m_i$ by introducing a tracer at the inlet point and following its occurrence at the outlet point over time. The latter can be effected, for example, by taking a small sample continuously at the point having the number 7 in FIG. 8. The tracer introduction point would appropriately be the point having the number 8 in FIG. 8.

In the case of dual-flow trays, it is possible to proceed in a corresponding manner. The volume element i selected here is appropriately that volume element which includes the liquid level on the mass transfer tray and the space below the mass transfer tray up to the start of the surface of the liquid level of the next mass transfer tray.

Figure 10:
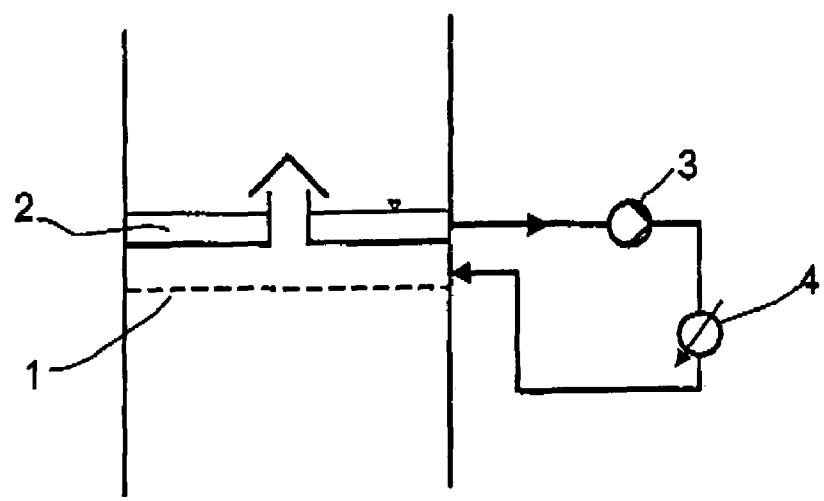
FIG. 10 shows a schematic diagram where the amount of liquid fed is conducted out of this collecting tray, the corresponding flow rate is determined and the liquid is subsequently recycled immediately above the sieve tray.

In order in this case to determine $\dot{m}_i$, a collecting tray may again be mounted above the sieve tray. The amount of liquid fed is conducted out of this collecting tray, the corresponding flow rate is determined and the liquid is subsequently recycled immediately above the sieve tray (cf. FIG. 10; 1=dual-flow tray, 2=collecting tray; 3=conveying pump; 4=flow meter).

Figure 11:
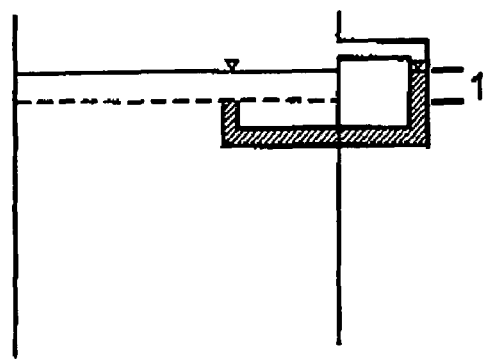
FIG. 11 shows a schematic diagram where the amount of liquid on the dual-flow tray may be determined, for example, by means of a pressure differential meter.

The amount of liquid on the dual-flow tray may be determined, for example, by means of a pressure differential meter according to FIG. 11 (U-tube manometer method). Using $\Delta p = \zeta \cdot g \cdot h_L$ ($h_L = 1$ in FIG. 11) where $\zeta$ is the mass density of the liquid phase, g the acceleration due to gravity and $h_L$ the liquid phase level on the dual-flow tray, $h_L$ can be read off directly and the amount of liquid on the dual-flow tray calculated.

The amount of liquid between two dual-flow trays can be determined by simultaneously sealing both dual-flow trays and determining the amount of liquid collecting on the lower tray. By means of chemical analysis, $m_i$ finally gives $m_{si}$.

In complete agreement, $m_{si}$ in the column bottom results from the bottoms level amount calculated from effluent and analysis of the composition of the bottoms liquid. $\dot{m}_i$ can be determined for level-regulated bottoms directly by measurement. The same applies to the circulation pump, and the circulation heat exchanger can be treated likewise. Column sections having bed-type packings or insert-type packings can be treated in a similar manner to mass transfer tray volume elements.

However, the $m_{si}$ and $m_i$ values within a separating column can also be determined semi empirically in very good approximation (cf., for example, Johann Stichlmair; Grundlagen der Dimensionierung des Gas/Flüssigkeit-Kontaktapparates [Guidelines for dimensioning gas/liquid contact apparatus], Bodenkolonne [Tray column], Verlag Chemie (1978) and Technische Fortschrittsberichte [Industrial progress reports], vol. 61, Grundlagen der Dimensionierung von Kolonnenböden [Guidelines for dimensioning column trays], by Dr.-Ing. Klaus Hoppe and Dr.-Ing. Manfred Mittelstrass, Magdeburg, Verlag Theodor Steinkopff, Dresden (1967)).

To this end, the particular tray temperature is initially determined, for example, over the different mass transfer trays. The composition is then determined of feeds and effluents from the separating column. Raoult's law (vapor-liquid equilibrium) combined with mass-energy balances are then used to calculate the concentration profiles in the column. The required liquid and gas flow rates then result from these. The $m_{si}$ values can be determined as follows. In separate experiments (gas flows from below and liquid is applied from above), the hydrodynamic behavior of the separating internals, for example of the mass transfer trays, is initially determined. These give $m_i$ values, from which the $m_{si}$ values finally follow by means of the concentration profiles.

The surprising result of the procedure according to the invention is that a reduction of $t_{ort}$ under otherwise substantially constant boundary conditions allows both the space-time yield and the degree of enrichment to be improved.

It will be appreciated that the procedure according to the invention may be combined with a procedure which comprises an integrated dissociation of the Michael adducts. At some points in this document, remarks have been made specifically on acrylic acid as the (meth)acrylic monomer. However, these remarks are generally also applicable to other (meth)acrylic monomers.

As is shown in the exemplary embodiment which follows, the procedure according to the invention at a $t_{ort}$ value of $\leq 10$ h even permits crude acrylic acid whose acrylic acid content is of values of a $\geq 95\%$ by weight to be removed from the product gas mixture of a (one- or two-stage) heterogeneously catalyzed propene and/or propane partial oxidation to acrylic acid whose acrylic acid content is from 5 to 15% by weight.

Figure 12:
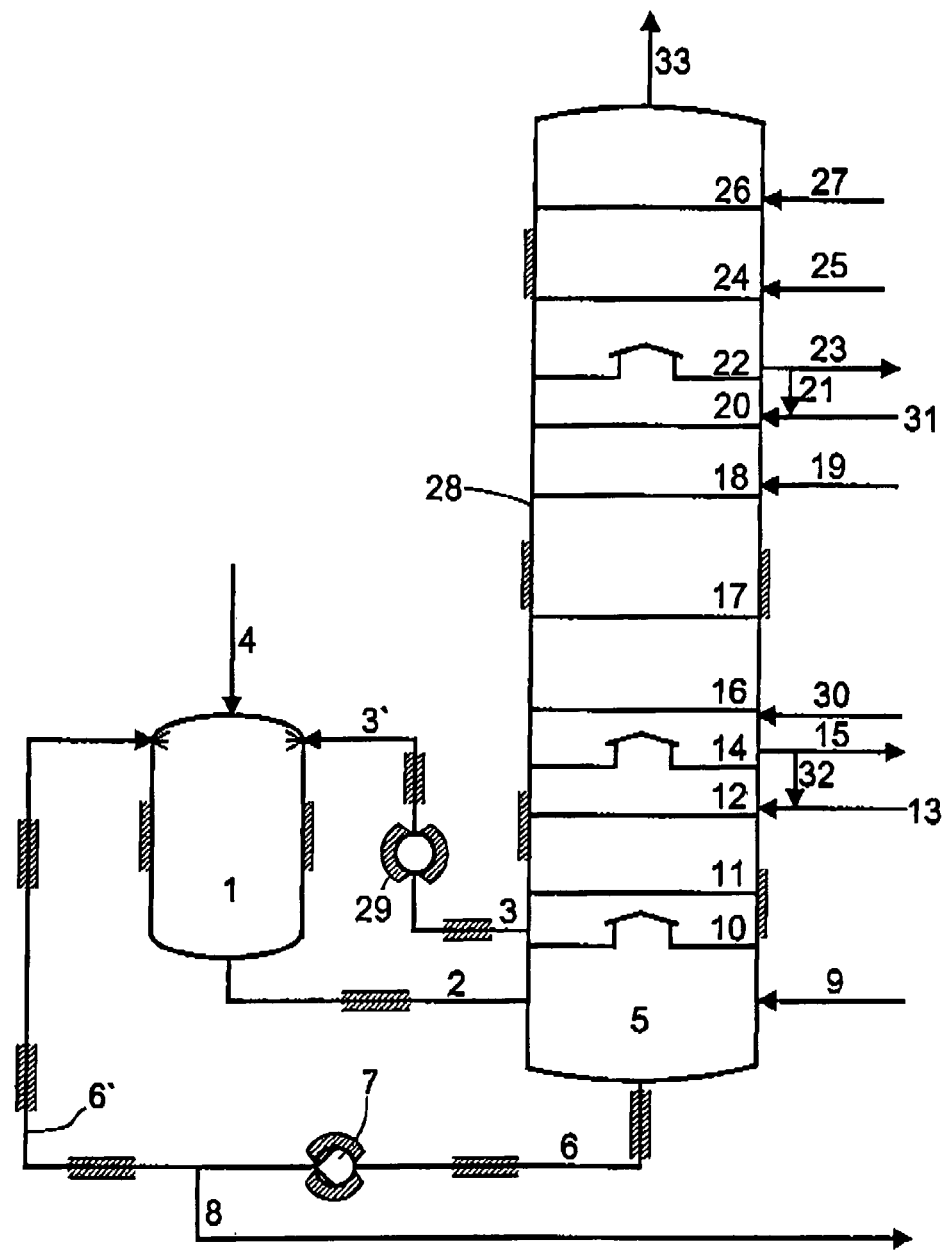
FIG. 12 shows a schematic diagram where the thermal separating process to be employed comprises the continuous steady-state operation of a thermal separating apparatus whose separating space is one including separating Internals.

The thermal separating process to be employed comprises the continuous steady-state operation of a thermal separating apparatus whose separating space is one including separating internals as shown schematically in FIG. 12.

It consists of a separating column 28 (whose separating internals are only mass transfer trays; from bottom to top, these are initially dual-flow trays and then hydraulically sealed crossflow trays which are finally superseded by valve trays; the separating column additionally contains collecting trays), a direct circulation evaporator 1 which is free of internals, which conveys by means of a pump 7 and a pump 29, and also pipelines 6,6', 3,3' and 2. A detailed description of such a separating column can be found in the documents DE-A 19 924 532, DE-A 10 247 240 and DE-A 10 243 625. It is appropriate from an application point of view for the number of theoretical plates to be from 15 to 30 and preferably 20. Although all elements beyond this separating space may be a constituent of the thermal separating apparatus employed overall, they do not belong to the inventive balance space, the separating space to be considered in accordance with the invention. An extension thereof increases $t_{ort}$ and does not contribute to the thermal separation to be considered. Use is thus made of the process according to the invention when the thermal separating process employed overall comprises a process according to the invention. The product gas mixture to be separated of the (one- or two-stage) heterogeneously catalyzed propene and/or propane partial oxidation to acrylic acid is at the same time the direct heat source of the direct circulation evaporator.

The example and comparative example which follow illustrate the present invention by way of example without restricting its general validity. Quite generally, the liquid phases which comprise (meth)acrylic monomers and occur in the process according to the invention comprise added polymerization inhibitors in a manner known per se.

Example and comparative example (the numerical addresses relate to FIG. 12; the region in FIG. 12 indicated by gray hatching is the separating space to be considered)

Comparative example (the steady state is described; suitable materials are, for example, stainless steel of the types 1.4639 or 1.4571)

A heterogeneously catalyzed gas phase partial oxidation of polymer grade propylene resulted in a product gas mixture having a temperature of 270° C. and the following contents being obtained:
11.80% by weight of acrylic acid,
0.284% by weight of acetic acid,
5.0984% by weight of water,
0.0275% by weight of formic acid,
0.0989% by weight of formaldehyde,
0.1473% by weight of acrolein,
0.0028% by weight of propionic acid,
0.0033% by weight of furfurals,
0.0014% by weight of allyl acrylate,
0.0005% by weight of allyl formate,
0.0038% by weight of benzaldehyde,
0.1350% by weight of maleic anhydride,
0.0112% by weight of benzoic acid,
0.0147% by weight of phthalic anhydride,
4.0324% by weight of oxygen.
1.8067% by weight of carbon dioxide,
0.5904% by weight of carbon monoxide,
0.5520% by weight of propane,
0.2696% by weight of propylene, and
75.1399% by weight of nitrogen.

No further constituents were detected. The product gas mixture (170 008 kg/h) is cooled in a direct circulation heat exchanger 1 operated in cocurrent to a temperature of 120.2° C. The direct circulation heat exchanger 1 operated in cocurrent is free of internals. It has a cylindrical shape. Its diameter is 2.2 m and its height is 15.5 m. The liquid phase to be heated in the direct circulation evaporator 1 is a mixture of bottoms liquid withdrawn from the bottom space 5 and of high boiler fraction which is withdrawn from the first collecting tray 10 completing the bottom space 5 of the separating column 28.

The amount of the bottoms liquid conducted into the direct circulation heat exchanger 1 is 247 305 kg/h and has the following contents (mass density=989.22 kg/m$^3$):
27.2977% by weight of acrylic acid,
0.1446% by weight of acetic acid,
0.6007% by weight of water,
0.0069% by weight of formic acid,
0.0007% by weight of formaldehyde,
0.0087% by weight of acrolein,
0.0149% by weight of propionic acid,
0.2041% by weight of furfurals,
0.0008% by weight of allyl acrylate,
0.0001% by weight of allyl formate,
0.2490% by weight of benzaldehyde,
4.4377% by weight of maleic anhydride,
0.7354% by weight of benzoic acid,
0.9605% by weight of phthalic anhydride,
19.5513% by weight of diacrylic acid,
40.1375% by weight of polyacrylic acid (Michael adduct),
0.4855% by weight of phenothiazine,
0.5560% by weight of monomethyl ether of hydroquinone (MEHQ),
4.6079% by weight of other high-boiling constituents, and
0.0002% by weight of oxygen.

The temperature of the bottoms liquid is 118.3° C. The vapor pressure is 1.48 bar. The amount of the high boiler fraction conducted into the direct circulation evaporator 1 is 63 009 kg/h and contains the following contents (mass density=969.94 kg/m$^3$):
90.4867% by weight of acrylic acid,
0.3672% by weight of acetic acid,
1.4207% by weight of water,
0.0142% by weight of formic acid,
0.0016% by weight of formaldehyde,
0.0109% by weight of acrolein,
0.0535% by weight of propionic acid,
0.6232% by weight of furfurals,
0.0025% by weight of allyl acrylate,
0.0002% by weight of allyl formate,
0.5317% by weight of benzaldehyde,
4.9046% by weight of maleic anhydride,
0.0401% by weight of benzoic acid,
0.0344% by weight of phthalic anhydride,
1.4102% by weight of diacrylic acid.
0.0201% by weight of phenothiazine,
0.0779% by weight of MEHQ, and
0.0004% by weight of oxygen.

The temperature of the high boiler fraction is 100.4° C. The vapor pressure is 1.48 bar.

The high boiler fraction is fed into the direct circulation evaporator 1 via a pipeline 3 of diameter 150 mm and length 10 m to a centrifugal pump 29 (liquid contents: 50 l) and from there via a pipeline 3' of diameter 150 mm and length 15 m into the direct circulation evaporator 1 (alternatively, the high boiler fraction may also be conducted by overflow into the bottom space and be conducted into the direct circulation evaporator as a constituent of the bottoms liquid).

The bottoms liquid which is withdrawn from the bottom space 5 is fed in an amount of 249 905 kg/h via a pipeline 6 having a diameter of 300 mm and a length of 10 m to a centrifugal pump 7 (liquid contents: 100 l) and conducted from there in an amount of 247 305 kg/h via a pipeline 6' of length 10 m and diameter 300 mm (pipeline diameters here always mean Internal diameter) Into the direct circulation evaporator 1.2300 kg/h of the bottoms liquid withdrawn are fed to dissociation and 300 kg/h of the bottoms liquid withdrawn are fed to the quench circuit I which will be described hereinbelow, in order to inhibit it against undesired polymerization (in both cases, it is fed via the pipeline 8). The mixture of bottoms liquid and high boiler fraction is sprayed in the direct circulation evaporator via a master nozzle (impingement nozzle according to WO 02/50011).

The biphasic mixture leaving the direct circulation evaporator 1 at a temperature of 120.2° C. is recycled into the bottom space 5 via the pipeline 2 (diameter: 1500 mm; length: 10 m).

The pressure in the bottom space 5 and in the direct circulation evaporator 1 is 1.48 bar. The height of the separating column 28 (a column for fractional condensation whose separating internals are only mass transfer trays; from bottom to top, these are initially dual-flow trays and then hydraulically sealed crossflow trays (Thormann trays) which are finally superseded by valve trays) is 54.3 m.

The internal diameter of the separating column 28 in the region of the Thormann trays is 6.5 m and otherwise 6.0 m.

The dissociation apparatus (which does not belong, for example, to the separating space), to which the 2300 kg/h of the bottoms liquid withdrawn from the bottom space 5 are fed, consists of a forced circulation flash evaporator and a dual-flow tray rectification column attached seamlessly to it. The number of dual-flow trays is 50.

The forced circulation flash evaporator consists of a dissociation vessel, a heat exchanger, a pump and the accompanying pipelines. The bottom effluent from the dissociation vessel is fed via a pipeline to a centrifugal pump which feeds it to a tube bundle heat exchanger. Subsequently, a portion of the heated liquid is recycled into the dissociation vessel via a pipeline. The other portion of the heated liquid is fed under viscosity(preferred), density or temperature control into a vessel to be described hereinbelow, in which methanol is mixed in.

Like the separating column 28, the rectification column is insulated from the environment. The internal diameter of the rectification column over all dual-flow trays is a uniform 2.4 m. Its height is 27 m. The dual-flow trays are arranged equidistantly (400 mm) in the rectification column. Their orifice ratio is a uniform 12%. Viewed from bottom to top, the hole diameter of the first eight dual-flow trays is a uniform 25 mm (hole arrangement corresponding to strict triangular pitch) and the hole diameter of all subsequent dual-flow trays is a uniform 14 mm (hole arrangement likewise corresponding to strict triangular pitch). The feed of the bottoms liquid to be subjected to the dissociation is to the eighth dual-flow tray (from the bottom).

20 000 kg/h of cycle gas which are removed at the top of the condensation column, and subsequently superheated and compressed, are fed (as support gas) to the dissociation vessel of the forced circulation flash evaporator (pressure=2.9 bar; temperature=160° C.).

The contents of the cycle gas are:
0.2288% by weight of acrylic acid,
0.0885% by weight of acetic acid,
2.6689% by weight of water,
0.0052% by weight of formic acid,
0.1724% by weight of acrolein,
0.0002% by weight of propionic acid,
0.0003% by weight of furfurals,
0.0012% by weight of allyl formate,
4.7392% by weight of oxygen,
2.1235% by weight of carbon dioxide,
0.6939% by weight of carbon monoxide,
0.6487% by weight of propane,
0.3169% by weight of propylene and
88.3123% by weight of nitrogen.

522 963 kg/h of liquid phase are constantly withdrawn from the dissociation vessel of the forced circulation flash evaporator at a temperature of 161° C. and a pressure of 1.71 bar. After passing through the heat exchanger, 522 246 kg/h of this are recycled into the dissociation vessel at a temperature of 166° C. and a pressure of 3 bar. The other 717 kg/h thereof are degassed, diluted with methanol and fed to residue incineration.

The dissociation gases forming in the dissociation vessel are conveyed into the attached rectification column by the support gas fed and rise therein in descending reflux liquid.

A gas mixture (comprising cycle gas and dissociation gas) is conducted out of the top of the rectification column in an amount of 33 129 kg/h at a temperature of 99.8° C. and a pressure of 1.60 bar, and cooled to a temperature of 63.3° C. a spray cooler operated in cocurrent (quench circuit I) by direct cooling, and partially condensed.

The gas mixture remaining after the direct cooling is recycled in an amount of 21 883 kg/h with the following contents via the line 9 into the bottom space 5 of the condensation column 28 (not immersed):
8.7215% by weight of acrylic acid,
0.0976% by weight of acetic acid,
2.5067% by weight of water,
0.0056% by weight of formic acid,
0.0001% by weight of formaldehyde,
0.1584% by weight of acrolein,
0.0019% by weight of propionic acid,
0.0017% by weight of furfurals,
0.0001% by weight of allyl acrylate,
0.0011% by weight of allyl formate,
0.0004% by weight of benzaldehyde,
0.0039% by weight of maleic anhydride,
4.3313% by weight of oxygen,
1.9407% by weight of carbon dioxide,
0.6342% by weight of carbon monoxide,
0.5929% by weight of propane,
0.2896% by weight of propylene and
80.7122% by weight of nitrogen.

The quench liquid I used is a mixture of the 300 kg/h of bottoms liquid withdrawn from the bottom space 5 and the condensate formed in the direct cooling in the quench circuit I. 104 207 kg/h of this mixture are cooled to 32° C. by indirect cooling and sprayed in the spray cooler I of the quench I. 11 546 kg/h of the same mixture are recycled as reflux liquid at a temperature of 63.3° C. to the uppermost dual-flow tray of the rectification column attached to the dissociation vessel.

The composition of the quench liquid I is:
93.7485% by weight of acrylic acid,
0.4937% by weight of acetic acid,
3.7513% by weight of water,
0.0143% by weight of formic acid,
0.0328% by weight of acrolein,
0.0207% by weight of propionic acid,
0.0240% by weight of furfurals,
0.0005% by weight of allyl acrylate,
0.0017% by weight of allyl formate,
0.0099% by weight of benzaldehyde,
0.1591% by weight of maleic anhydride,
0.0192% by weight of benzoic acid,
0.0250% by weight of phthalic anhydride,
0.5083% by weight of diacrylic acid,
1.0429% by weight of polyacrylic acid,
0.0126% by weight of phenothiazine,
0.0146% by weight of MEHQ,
0.1198% by weight of other high-boiling constituents, and
0.0011% by weight of oxygen.

A centrifugal drop separator is integrated into the bottom space 5 of the condensation column 28 and prevents droplets of the bottoms liquid being entrained upward out of the bottom space. At the lower end of the bottom space 5 is installed what is known as a Chinese hat for improved gas/liquid separation. The amount of liquid phase retained (the liquid holdup) in the system, composed of bottom space 5, pipeline 6 to the circulation pump 7, circulation pump 7, pipeline 6' from the circulation pump 7 to the direct circulation evaporator 1, direct circulation evaporator 1 and pipeline 2 from the direct circulation evaporator 1 into the bottom space 5, is 80 m$^3$.

As already mentioned, the bottom space of the separating column 28 is completed at a column height (like all heights, calculated from the column bottom) of 7.80 m by a first collecting tray 10 (chimney tray having 16 approximately uniformly distributed roofed chimneys; chimney diameter: 600 mm; chimney height: 1 m).

The collecting tray 10 has a double-walled configuration with 2° gradients toward the interior and having a central takeoff cup and takeoff nozzle (DN~200). The free gas cross section is approx. 30%.

As already mentioned, 63 009 kg/h of liquid (T=100.4° C., p=1.48 bar) are withdrawn from this first collecting tray and conducted into the direct circulation evaporator 1 by means of the centrifugal pump 29. The liquid volume of the collecting tray 10 is 2 m$^3$ (the liquid holdup in the system, composed of this liquid volume on the collecting tray 10, pipeline 3 to the circulation pump 29, circulation pump 29 and pipeline 3' from the circulation pump 29 to the direct circulation evaporator 1, is 3 m$^3$).

2.0 m above the first collecting tray 10 is disposed the first (11) of initially 15 dual-flow trays. These dual-flow trays (hole diameter a uniform 14 mm, hole number a uniform 33 678, orifice ratio a uniform 18%) are mounted equidistantly with a tray separation of 380 mm. The passages consist of circular orifices of a uniform diameter of 14 mm, with the punched burr pointing downward in the separating column. The arrangement of the centers of the passage circles follows strict triangular pitch.

The fifteenth dual-flow tray (12) is configured as a distributor tray. For this purpose, two insert tubes (DN-150) having 40 drain drillholes (diameter: 15 mm) per insert tube are mounted above it.

The first series of dual-flow trays is completed by a second collecting tray 14 (chimney tray having 16 approx. uniformly distributed roofed chimneys; chimney height approx. 1.70 m, central takeoff cup having lateral takeoff nozzles (DN~250), free gas cross section of ~30%) according to WO 03 047714, which is mounted 1.50 m above the last dual-flow tray.

From this second collecting tray 14, crude acrylic acid at a temperature of 101.2° C. is withdrawn continuously via the line 15 at 1.47 bar (mass density=956.99 kg/m$^3$) and has the following contents:
96.8011% by weight of acrylic acid,
0.4598% by weight of acetic acid,
1.4762% by weight of water,
0.0137% by weight of formic acid,
0.0015% by weight of formaldehyde,
0.0087% by weight of acrolein,
0.0647% by weight of propionic acid,
0.2856% by weight of furfurals,
0.0027% by weight of allyl acrylate,
0.0002% by weight of allyl formats,
0.0744% by weight of benzaldehyde,
0.2381% by weight of maleic anhydride,
0.5430% by weight of diacrylic acid,
0.0120% by weight of phenothiazine,
0.0180% by weight of MEHQ, and
0.0004% by weight of oxygen.

The liquid volume on the second collecting tray 14 is 10 m$^3$. 455 855 kg/h of the crude acrylic acid withdrawn from the second collecting tray 14 are heated to 111.2° C. by indirect heat exchange and recycled into the condensation column 28 via the line 30 immediately below the dual-flow tray 16 following above the second collecting tray (p=1.50 bar).

89 978 kg/h of the crude acrylic add withdrawn from the second collecting tray form the stream containing (meth) acrylic monomers which has been removed in the separating space, and are cooled to a temperature of 29° C. in a plurality of stages by indirect heat exchange (preferably heat-integrated against the mother liquor to be recycled into the separating column 28). 1144 kg/h of water (25° C.) water are then added to the cooled crude acrylic acid. The resulting mixture is cooled to 20° C. by repeated indirect heat exchange and then conducted into from two to three cooling disk crystallizers.

These are each a trough in which from 20 to 24 wiped circular cooling plates (which are flowed through internally by a cooling medium (mixture of water and glycol; proportion of glycol=10 to 50% by weight preferably 25 to 35% by weight)) are arranged hanging in succession at an equidistant separation of from 20 to 40 cm (plate diameter typically from 2 to 4 m, preferably from 2.5 to 3 m). The cooling medium is conveyed in countercurrent to the crystallizing mixture through the crystallizer from cooling disk to cooling disk. However, It may also be conducted over the cooling plates divided into 2 or 3 parallel streams. The entrance temperature of the cooling medium (of the brine) is from −2 to +5° C. The exit temperature is from 2 to 7° C. higher. The wiping of the cooling plates suppresses the formation of a crystal layer. The crude acrylic acid having increased water content is conducted continuously (pumped or controlled by overflows) from back to front through the crystallizer. The monophasic crude acrylic acid having increased water content thickens (residence time from 0.5 to 4 h, preferably from 1.5 to 2.5 h) to a biphasic suspension comprising acrylic acid crystals as the solid phase and having a temperature of from 6 to 11° C. and a solids content at the exit of from 20 to 35% by weight The speed of the wipers is from 2 to 15 revolutions per minute, preferably from 4 to 10 revolutions per minute. The shaft which drives the wipers and passes through the centers of the cooling disks is sealed with water-washed stuffing box packings(packing braids made of Teflon or graphite).

On the circumference of the cooling disks where it is not possible to wipe, a hollow profile (e.g. in the simplest embodiment a tube) is mounted (e.g. welded on) and is heated by means of a second heat carrier (e.g. likewise water/glycol mixture) (to a temperature above the crystallization temperature; usually within the temperature range from 8 to 20° C., preferably from 10 to 140° C.). These circumference heaters are flowed through in parallel by the second heat carrier.

Furthermore, the wipers are preferably segmented in the radial direction ($\geq 2, \leq 6$ segments in general). The specific pressing force of the wipers perpendicular to the cooling surface in the installed state is from 1 to 10 N, preferably from 3 to 5 N, per cm of active wiping edge length. In addition to the wipers, the shaft drives paddles (there are advantageously two each in a symmetrical arrangement between two cooling disks and before the first and last cooling disk) which bring about improved mixing.

The nature of the cooling plate surface and the alignment of the wipers are such that the distance of the wipers from the cooling plate surface at no point exceeds 6 mm (it is favourable to operate with the aforementioned distance at no point exceeding 4 or 2 or 1 mm, or with the wipers being in contact at each point; it has been found to be particularly advantageous for there to be contact at the outer radius).

In the last section of the crystallizer in the conveying direction of the suspension (preferably beyond the last cooling disk), the suspension is conducted via an attached tube (appropriately mounted immersed; alternatively, the suspension may flow via an overflow weir into a stirred reservoir, whence the washing columns are charged) to hydraulic melt-washing columns, as described in DE-A 10 156 016 and DE-A 10 223 058, in order to separate the mother liquor from the suspension crystals. The washing columns are charged with crystal suspension by means of a centrifugal pump or a rotary piston pump. The control stream pump is likewise configured as a rotary piston pump or as a centrifugal pump having a regulating valve. The pressure at the lower end of a washing column is typically $\geq 100$ mbar and $\leq 5$ bar lower than the pressure at the top of the washing column. The top pressure is generally up to 6 bar, usually from 0.5 to 4 bar. The blade speed is usually at values of >0 and $\leq 100$/min, or $\leq 60$/min. The temperature in the melt circuit is normally from 13 to 16° C. The filtration front is detected according to DE-A 10 036 880 by from 2 to 4 optical sensors. The washing front is controlled by means of temperature measurement in the crystal bed.

The total height of the crystal bed is typically from 300 to 1500 mm, usually from 400 to 1000 mm. The washing front is typically from 10 to 400 mm, usually from 20 to 250 mm, above the blade. Useful melt circuit pumps are a centrifugal pump with product-side washing of the shaft seal (slip-ring seal) or a magnet-coupled pump with increased washing of the sliding bearings. The circulation amount in the melt circuit is from 2 to 30 m³/h. usually from 5 to 20 m³/h, per metric tonne of purified crystals removed with the blade. The melt circuit is stabilized by means of from 100 to 300 ppm by weight of MEHQ. In addition, air is introduced into the melt circuit and its excess (=the proportion not dissolved in the wash melt) is removed by a gas separator before entry of the wash melt into the washing column.

[(a) To prepare esterification-grade acrylic acid, it is sufficient to carry out the removal of the suspension crystals by means of a centrifuge (e.g. a 2- or 3-stage pusher centrifuge) instead of in a melt-washing column. Suitable screen gap widths are from 150 to 300 mm; centrifugal accelerations which can be used are from 500 to 900 g, usually from 600 to 800 g; suitable stroke rates are from 40 to 80 strokes/min.

Preference is given to washing the crystals removed from the 2nd or 3rd stage of the centrifuge with from 0.15 to 0.3 kg of washing liquid per kg of crystals. The temperature of the washing liquid is from 15 to 30° C., preferably from 20 to 30° C. To avoid deposits, the solids discharge chute of the centrifuge is flushed with flushing liquid heated to from 15 to 30° C. Flushing and washing liquid are preferably molten crystals removed and washed by the centrifuge. To avoid deposits and encrustations, it is appropriate to heat the centrifuge housing, the suspension feed tube and the washing liquid feed tube to a temperature $\geq 15°$ C. and $\leq 40°$ C. The product space of the centrifuge is appropriately inertized with nitrogen or with a mixture of air and nitrogen. The shaft seal is purged with gas (e.g. nitrogen or a mixture of air and nitrogen) or with water.

(b) Alternatively to the suspension crystallization, it is also possible to use a layer crystallization (e.g. falling-film crystallization according to EP-A 616 998 or tube with full flow-through) having 3 or more (e.g. 3 or 4) purification stages. Instead of recycling the mother liquor from a following purification stage into a preceding purification stage, it is also possible to recycle them together into the condensation column.]

From the melt circuits which are stabilized by the addition of 3 kg/h of MEHQ, 18 538 kg/h of glacial acrylic acid having the following contents are withdrawn:
99.8335% by weight of acrylic acid,
0.0970% by weight of acetic acid,
0.0334% by weight of water,
0.026% by weight of propionic acid,
0.0001% by weight of furfurals,
0.0001% by weight of maleic anhydride,
0.0003% by weight of diacrylic acid, and
0.0150% by weight of MEHQ.

It is outstandingly suitable for preparing superabsorbents based on poly-sodium acrylate.

13 kg/h of PTZ are dissolved in 829 kg/h of glacial acrylic acid to prepare an inhibitor solution I. 19 kg/h of MEHQ are dissolved in 30 kg/h of inhibitor solution I to form the inhibitor solution II.

The mother liquor removed in the washing columns is initially conducted into a heatable collecting vessel and from there into a tank. From this tank, it is recycled heated to 90° C. with heat integration in an amount of 71 759 kg/h via the line 13 to the fifteenth dual-flow tray 12 of the condensation column 28 (counted from below). The contents of this recycled mother liquor are as follows:
94.4349% by weight of acrylic acid,
0.5504% by weight of acetic acid,
3.4362% by weight of water,
0.0172% by weight of formic acid,
0.0018% by weight of formaldehyde.
0.0109% by weight of acrolein,
0.0756% by weight of propionic acid,
0.3580% by weight of furfurals,
0.0034% by weight of allyl acrylate,
0.0003% by weight of allyl formate,
0.0933% by weight of benzaldehyde,
0.2986% by weight of maleic anhydride,
0.6808% by weight of diacrylic acid,
0.0150% by weight of phenothiazine.
0.0233% by weight of MEHQ, and
0.0005% by weight of oxygen.

In addition, 15 224 kg/h of crude acrylic acid withdrawn from the collecting tray 14 are recycled to the dual-flow tray 12 (32).

2.9 m above the second collecting tray 14 in the condensation column 28 is disposed the first (16) of 21 further dual-flow trays of the type already described (hole diameter again a uniform 14 mm, but hole number a uniform 32 020 and orifice ratio a uniform 17.4%) which are again arranged equidistantly with a tray separation of 380 mm. The reflux from the Thormann tray region into the dual-flow tray region is via a distributor system integrated into the column. Alternatively, reflux could also be effected by conducting the reflux liquid out of the condensation column below the lowermost Thormann tray by means of a pump and recycling it into the condensation column via two (or more) Insert tubes which are mounted above the uppermost dual-flow tray.

800 mm above the last dual-flow tray, the condensation column begins to widen conically. 500 mm above the last dual-flow tray, this widening ends at a column internal diameter of 6.50 m.

At this height, i.e. 1.50 m above the last dual-flow tray (17), begins an equidistant (tray separation=500 mm) arrangement of 28 conventional, single-flow Thormann trays. The Thormann trays are configured in such a way that the arrangement of the transport slots in the hoods of the Thormann trays in successive channels in the crossflow direction each generate a mutually opposed flow direction of the liquid.

The orifice ratio of the Thormann trays is 14%. The ratio of chimney surface area to slot exit surface area is 0.8. The chimney height and the height of the overflow weir are 40 mm. The bottom clearance of the bubble-cap (distance between lower edge of slot and tray) is 10 mm. The slot height is 15 mm. The angle between obliquely angled slot and longitudinal edge of the hood is 30 degrees. The maximum length of the longitudinal edge of the hood is 800 mm. In the peripheral region of the column, the hood length reduces to 200 mm for reasons of adaptation to the roundness of the column. The distance between two hoods disposed on a line in the crossflow direction is 66 mm. The drain surface area of the downcorner is 1.5% based on the cross-sectional area of the tray. The breadth between the two lower longitidunal edges of a hood is 64 mm.

At the height of the uppermost Thormann tray 20, the separating column begins to narrow again conically. 700 mm above the uppermost Thormann tray, this narrowing is complete and the column internal diameter has contracted again to 6.0 m.

1.70 m above the uppermost Thormann tray is disposed the third collecting tray 22 (chimney tray having 16 approx. uniformly distributed roofed chimneys, chimney height=1.50 m). The liquid volume on the collecting tray 3 is 8 m³ (mass density=964.38 kg/m³).

From the third collecting tray are withdrawn 533 617 kg/h of acid water at a temperature of 68.6° C. and at a pressure of 1.24 bar via the line 23.

The contents of the acid water are:
11.3387% by weight of acrylic acid,
4.1574% by weight of acetic acid,
81.6277% by weight of water,
0.5256% by weight of formic acid,
2.3082% by weight of formaldehyde,
0.0154% by weight of acrolein,
0.0089% by weight of propionic acid.
0.0024% by weight of furfurals,
0.0135% by weight of allyl formate,
0.0001% by weight of MEHQ, and
0.0021% by weight of oxygen.

29 015 kg/h of the acid water withdrawn (68.6° C.) are recycled (21) together with the inhibitor solution II (31) to the uppermost Thormann tray (20).

812 kg/h of the inhibitor solution I are recycled (at a temperature of 25° C. and a pressure of 3 bar via the line 19) to the 19th Thormann tray (18) (viewed from below). 7282 kg/h of the acid water withdrawn are fed to incineration.

298 392 kg/h of the acid water withdrawn are recycled (3 bar) via the line 25 at a temperature of 29° C. to the sixth (24) of the valve trays to be described below (counted from below). In the event of foam formation, it has been found to be appropriate to add antifoams (for example alkoxylated alcohols such as Dekresa® SD 23 or mixtures of fatty acid, polyglycol, emulsifiers and paraffinic mineral oil mixture such as Nalco® 71-D-5) at the third collecting tray (for example in an amount of 30 ml/h).

198 928 kg/h of the add water withdrawn are recycled via the line 27 at a temperature of 22.5° C. (p=3 bar) to the uppermost (26) of the valve trays to be described below.

2300 mm above the third collecting tray 22 are mounted 11 double-flow valve trays in the condensation column 28 in equidistant arrangement (tray separation=500 mm). The height of the overflow weir is 35 mm. The office ratio is 18% and the sum of the drain surface areas of the downcorners of two successive valve trays is 10% of the column cross-sectional areas. The valves used were VV12 valves from Stahl, DE, Viernheim.

The pressure at the top of the column 28 is 1.2 bar.

At the top of the column, 164 650 kg/h of offgas (33) leave the separating column 28 via a demister at a temperature of 33.5° C. and have the following contents:
0.2288% by weight of acrylic add,
0.0885% by weight of acetic acid,
2.6689% by weight of water,
0.0052% by weight of formic acid,
0.1724% by weight of acrolein,
0.0002% by weight of propionic acid,
0.0003% by weight of furfurals,
0.0012% by weight of allyl formate,
2.1235% by weight of $CO_2$,
0.6939% by weight of CO,
0.6487% by weight of propane,
0.3169% by weight of propylene,
4.7392% by weight of $O_2$, and
88.3123% by weight of $N_2$.

In an indirect heat exchanger, the offgas is heated to 38° C. and 91 196 kg/h of this offgas are subsequently conducted through a cycle gas compressor (for example a radial compressor) as diluent gas into the gas phase oxidation and into the dissociation, and 73 455 kg/h of the offgas are fed to incineration.

Overall, the following individual streams are conducted into the separating space and have the following acrylic acid contents:
170 008 kg/h of product gas mixture of the gas phase partial oxidation of propylene having an acrylic acid content of 11.8% by weight;
21 883 kg/h via the line 9 and having an acrylic acid content of 8.7215% by weight;
15 224 kg/h via the line 32 and having an acrylic acid content of 96.8011% by weight;
71 759 kg/h via the line 13 and having an acrylic acid content of 94.4349% by weight;
455 855 kg/h via the line 30 and having an acrylic acid content of 96.7887% by weight;
81.2 kg/h via the line 19 and having an acrylic acid content of 98.3360% by weight;
29 015 kg/h via the line 21 and having an acrylic acid content of 11.3387% by weight; and 49 kg/h via the line 31 and having an acrylic add content of 60.2057% by weight.

This means that overall a (theoretically generated) stream of 764 605 kg/h is conducted into the separating space and has an acrylic acid content of 71.907% by weight. This means that X=28.09% by weight.

The stream which is conducted out of the separating space with the highest proportion by weight of acrylic acid is the crude acrylic acid removed from the second collecting tray which has an acrylic acid content of 96.8011% by weight of acrylic acid. This means that Y=3.20% by weight and X:Y=8.78.

The total volume of the separating space filled with liquid phase is 167.5 m³. The temperature of this liquid phase is, at least in places, 120.2° C. (for example in the direct circulation heat exchanger).

Table 1 which follows shows the selected volume elements i ("tray i" represents the volume element i which includes the liquid phase present on the mass transfer tray i and the liquid phase present in the volume below the mass transfer tray i (excluding the liquid phase disposed on the tray below)). The numbering of the mass transfer trays numbers from bottom to top in the separating column.

Table 1 also contains the temperatures determined $T_i$, the values determined $m_{si}$ and the mass flow rates determined $\dot{m}_i$.

Table 1 also contains the individual values $t_i^* = 2^A m_{si}/\dot{m}_i$.

TABLE 1

| Volume element i | $m_{si}$ (kg) | $\dot{m}_i$ (kg/h) | $t_i^*$ (h) | $T_i$ (° C.) |
|---|---|---|---|---|
| Total volume of pipelines 6, 6' and 2, and pump 7, bottom space 5 and direct circulation evaporator 1 | 21 828.8 | 2300.0 | 33.74320 | 118.3 |
| Collecting tray 1 including pipelines 3 and 3' | 2663.6 | 63 009.2 | 0.043353 | 100.4 |
| Tray 1 | 301.9 | 63 009.2 | 0.004913 | 100.4 |
| Tray 2 | 303.7 | 68 968.9 | 0.004456 | 100.2 |
| Tray 3 | 305.6 | 74 928.7 | 0.004072 | 100.0 |
| Tray 4 | 307.5 | 80 888.4 | 0.003744 | 99.8 |
| Tray 5 | 309.3 | 86 848.2 | 0.003461 | 99.6 |
| Tray 6 | 311.1 | 92 807.9 | 0.003214 | 99.4 |
| Tray 7 | 311.6 | 92 865.4 | 0.003123 | 99.0 |
| Tray 8 | 312.2 | 92 923.0 | 0.003035 | 98.5 |
| Tray 9 | 312.7 | 92 980.5 | 0.002949 | 98.1 |
| Tray 10 | 313.2 | 93 038.1 | 0.002866 | 97.7 |
| Tray 11 | 313.7 | 96 839.1 | 0.002873 | 98.3 |
| Tray 12 | 314.1 | 100 640.1 | 0.002885 | 98.9 |
| Tray 13 | 314.6 | 104 441.1 | 0.002901 | 99.5 |

TABLE 1-continued

| Volume element i | $m_{st}$ (kg) | $\dot{m}_i$ (kg/h) | $t_i^*$ (h) | $T_i$ (° C.) |
|---|---|---|---|---|
| Tray 14 | 315.0 | 108 242.1 | 0.002920 | 100.0 |
| Tray 15 | 315.5 | 112 043.1 | 0.002944 | 100.6 |
| Collecting tray 2 | 9292.9 | 115 844.1 | 0.087376 | 101.2 |
| Tray 16 | 265.8 | 115 844.1 | 0.002499 | 101.2 |
| Tray 17 | 266.1 | 118 186.3 | 0.002441 | 101.2 |
| Tray 18 | 266.3 | 120 528.5 | 0.002385 | 101.1 |
| Tray 19 | 266.6 | 122 870.7 | 0.002332 | 101.0 |
| Tray 20 | 266.9 | 125 212.9 | 0.002280 | 101.0 |
| Tray 21 | 267.2 | 127 555.1 | 0.002230 | 100.9 |
| Tray 22 | 267.2 | 127 588.1 | 0.002223 | 100.9 |
| Tray 23 | 267.2 | 127 621.0 | 0.002215 | 100.8 |
| Tray 24 | 267.2 | 127 654.0 | 0.002207 | 100.8 |
| Tray 25 | 267.3 | 127 686.9 | 0.002199 | 100.7 |
| Tray 26 | 267.3 | 127 719.9 | 0.002192 | 100.7 |
| Tray 27 | 267.3 | 127 752.9 | 0.002184 | 100.6 |
| Tray 28 | 267.3 | 127 785.8 | 0.002176 | 100.6 |
| Tray 29 | 267.3 | 127 760.1 | 0.002165 | 100.5 |
| Tray 30 | 267.3 | 127 734.3 | 0.002154 | 100.4 |
| Tray 31 | 267.3 | 127 708.5 | 0.002144 | 100.3 |
| Tray 32 | 267.3 | 127 682.8 | 0.002133 | 100.3 |
| Tray 33 | 267.3 | 127 657.0 | 0.002122 | 100.2 |
| Tray 34 | 267.2 | 127 631.3 | 0.002111 | 100.1 |
| Tray 35 | 267.2 | 127 605.5 | 0.002101 | 100.0 |
| Tray 36 | 267.1 | 127 381.4 | 0.002065 | 99.8 |
| Tray 37 | 1428.6 | 127 157.2 | 0.010862 | 99.5 |
| Tray 38 | 1428.1 | 126 933.1 | 0.010679 | 99.2 |
| Tray 39 | 1427.6 | 126 709.0 | 0.010498 | 99.0 |
| Tray 40 | 1422.6 | 125 231.0 | 0.009699 | 97.7 |
| Tray 41 | 1417.4 | 123 752.9 | 0.008960 | 96.5 |
| Tray 42 | 1371.5 | 115 844.1 | 0.006492 | 91.3 |
| Tray 43 | 1304.0 | 107 584.7 | 0.005208 | 87.8 |
| Tray 44 | 1236.7 | 99 325.3 | 0.004190 | 84.3 |
| Tray 45 | 994.1 | 77 092.8 | 0.003002 | 79.0 |
| Tray 46 | 869.1 | 67 710.3 | 0.002705 | 77.5 |
| Tray 47 | 744.5 | 58 327.8 | 0.002436 | 76.1 |
| Tray 48 | 684.1 | 54 345.3 | 0.002313 | 75.6 |
| Tray 49 | 624.0 | 50 362.8 | 0.002191 | 75.0 |
| Tray 50 | 357.7 | 46 380.3 | 0.001313 | 74.5 |
| Tray 51 | 328.9 | 43 818.9 | 0.001247 | 74.1 |
| Tray 52 | 300.3 | 41 257.4 | 0.001180 | 73.7 |
| Tray 53 | 271.8 | 38 696.0 | 0.001111 | 73.4 |
| Tray 54 | 253.0 | 37 314.8 | 0.001054 | 73.1 |
| Tray 55 | 234.3 | 35 933.6 | 0.000997 | 72.9 |
| Tray 56 | 215.7 | 34 552.4 | 0.000938 | 72.7 |
| Tray 57 | 202.2 | 33 699.1 | 0.000890 | 72.5 |
| Tray 58 | 188.8 | 32 845.8 | 0.000841 | 72.3 |
| Tray 59 | 175.3 | 31 992.5 | 0.000791 | 72.1 |
| Tray 60 | 164.2 | 31 391.2 | 0.000744 | 71.9 |
| Tray 61 | 153.1 | 30 789.8 | 0.000696 | 71.6 |
| Tray 62 | 142.0 | 30 188.4 | 0.000648 | 71.4 |
| Tray 63 | 124.3 | 29 626.2 | 0.000524 | 70.0 |
| Tray 64 | 106.6 | 29 064.0 | 0.000416 | 68.6 |
| Collecting tray 3 | 889.1 | 533 617.0 | 0.000189 | 68.6 |
| Tray 65 | 222.3 | 533 617.0 | 0.000047 | 68.6 |
| Tray 66 | 221.7 | 529 532.3 | 0.000038 | 65.2 |
| Tray 67 | 221.1 | 525 447.6 | 0.000030 | 61.8 |
| Tray 68 | 222.0 | 520 416.7 | 0.000020 | 55.9 |
| Tray 69 | 222.9 | 515 385.9 | 0.000014 | 50.0 |
| Tray 70 | 223.4 | 504 553.3 | 0.000013 | 48.6 |
| Tray 71 | 201.5 | 204 568.8 | 0.000025 | 47.2 |
| Tray 72 | 202.2 | 203 298.7 | 0.000021 | 44.6 |
| Tray 73 | 202.8 | 202 028.6 | 0.000018 | 42.0 |
| Tray 74 | 203.4 | 200 478.3 | 0.000014 | 37.8 |
| Tray 75 | 204.1 | 198 928.0 | 0.000010 | 33.5 |

This results in a $t_{ort}$ of 34.06 h.

At this $t_{ort}$, the stream containing (meth)acrylic monomers which is removed in the separating space and has the highest proportion by weight of 89 978 kg/h of crude acrylic acid having an acrylic acid content of 96.8011% by weight.

Example (the steady state is described)

Substantially everything is carried out as in the comparative example. except that the volume of the bottom space 5 is reduced to the extent that the liquid holdup in the bottom space is 59 974.2 kg less than in the comparative example (the liquid holdup in the volume element 1, consisting of the pipelines 6, 6' and 2, and of the pump 7, bottom space 5 and direct circulation evaporator 1, is thus 79 965.6 kg in the comparative example and 19 991.4 kg in the example).

In addition, the amount of high boiler fraction removed from the first collecting tray 10 and fed to the direct circulation evaporator 1 is 74 083 kg/h instead of 63 009 kg/h.

This change is required in order, in the direct circulation evaporator 1, to achieve the boiling temperature which falls in the bottom space 5 as a consequence of the changed composition of the bottoms liquid.

Table 2 which follows is the analog of table 1 for the example.

TABLE 2

| Volume element i | $m_{st}$ (kg) | $\dot{m}_i$ (kg/h) | $t_i^*$ (h) | $T_i$ (° C.) |
|---|---|---|---|---|
| Total volume of pipelines 6, 6' and 2, and pump 7, bottom space 5 and direct circulation evaporator 1 | 8780.0 | 2300.0 | 8.47136 | 111.5 |
| Collecting tray 1 including pipelines 3 and 3' | 2696.2 | 74 083.0 | 0.03711 | 100.3 |
| Tray 1 | 305.6 | 74 083.0 | 0.00421 | 100.3 |
| Tray 2 | 307.0 | 77 918.5 | 0.00397 | 100.1 |
| Tray 3 | 308.3 | 81 754.1 | 0.00375 | 99.9 |
| Tray 4 | 309.7 | 85 589.6 | 0.00356 | 99.8 |
| Tray 5 | 311.1 | 89 425.2 | 0.00338 | 99.6 |
| Tray 6 | 312.4 | 93 260.7 | 0.00322 | 99.4 |
| Tray 7 | 312.8 | 93 255.4 | 0.00313 | 99.0 |
| Tray 8 | 313.2 | 93 250.0 | 0.00304 | 98.6 |
| Tray 9 | 313.6 | 93 244.7 | 0.00295 | 98.1 |
| Tray 10 | 314.0 | 93 239.3 | 0.00287 | 97.7 |
| Tray 11 | 314.4 | 97 316.8 | 0.00287 | 98.3 |
| Tray 12 | 314.8 | 101 394.3 | 0.00288 | 98.9 |
| Tray 13 | 315.2 | 105 471.8 | 0.00288 | 99.5 |
| Tray 14 | 315.6 | 109 549.3 | 0.00290 | 100.1 |
| Tray 15 | 316.0 | 113 626.8 | 0.00291 | 100.7 |
| Collecting tray 2 | 9305.6 | 117 704.3 | 0.08632 | 101.3 |
| Tray 16 | 266.1 | 117 704.3 | 0.00247 | 101.3 |
| Tray 17 | 266.4 | 119 728.4 | 0.00242 | 101.2 |
| Tray 18 | 266.7 | 121 752.6 | 0.00237 | 101.1 |
| Tray 19 | 266.9 | 123 776.7 | 0.00232 | 101.1 |
| Tray 20 | 267.2 | 125 800.8 | 0.00228 | 101.0 |
| Tray 21 | 267.4 | 127 825.0 | 0.00223 | 101.0 |
| Tray 22 | 267.5 | 127 857.5 | 0.00223 | 100.9 |
| Tray 23 | 267.5 | 127 890.0 | 0.00222 | 100.9 |
| Tray 24 | 267.5 | 127 922.6 | 0.00221 | 100.8 |
| Tray 25 | 267.5 | 127 955.1 | 0.00221 | 100.8 |
| Tray 26 | 267.5 | 127 987.6 | 0.00220 | 100.7 |
| Tray 27 | 267.5 | 128 020.1 | 0.00219 | 100.7 |
| Tray 28 | 267.5 | 128 052.7 | 0.00218 | 100.6 |
| Tray 29 | 267.5 | 128 032.7 | 0.00217 | 100.6 |
| Tray 30 | 267.5 | 128 012.7 | 0.00216 | 100.5 |
| Tray 31 | 267.5 | 127 992.7 | 0.00215 | 100.4 |
| Tray 32 | 267.5 | 127 972.7 | 0.00214 | 100.4 |
| Tray 33 | 267.5 | 127 952.7 | 0.00213 | 100.3 |
| Tray 34 | 267.5 | 127 932.8 | 0.00212 | 100.2 |
| Tray 35 | 267.5 | 127 912.8 | 0.00211 | 100.2 |
| Tray 36 | 267.5 | 127 726.1 | 0.00208 | 99.9 |
| Tray 37 | 1430.9 | 127 539.4 | 0.01098 | 99.7 |
| Tray 38 | 1430.7 | 127 352.6 | 0.01081 | 99.4 |
| Tray 39 | 1430.5 | 127 165.9 | 0.01065 | 99.2 |
| Tray 40 | 1427.2 | 125 904.8 | 0.00993 | 98.1 |
| Tray 41 | 1423.7 | 124 643.7 | 0.00926 | 97.0 |
| Tray 42 | 1386.2 | 117 704.3 | 0.00689 | 92.3 |
| Tray 43 | 1327.1 | 110 026.5 | 0.00553 | 88.8 |
| Tray 44 | 1267.4 | 102 348.7 | 0.00445 | 85.2 |
| Tray 45 | 1035.0 | 80 031.0 | 0.00311 | 79.4 |
| Tray 46 | 905.3 | 70 048.9 | 0.00279 | 77.9 |
| Tray 47 | 775.9 | 60 066.8 | 0.00250 | 76.3 |
| Tray 48 | 711.2 | 55 777.7 | 0.00237 | 75.7 |
| Tray 49 | 646.8 | 51 488.6 | 0.00224 | 75.1 |
| Tray 50 | 369.4 | 47 199.5 | 0.00134 | 74.5 |
| Tray 51 | 339.0 | 44 494.6 | 0.00127 | 74.2 |
| Tray 52 | 308.8 | 41 789.7 | 0.00120 | 73.8 |
| Tray 53 | 278.6 | 39 084.7 | 0.00113 | 73.4 |

TABLE 2-continued

| Volume element i | $m_{sl}$ (kg) | $\dot{m}_i$ (kg/h) | $t_i^*$ (h) | $T_i$ (° C.) |
|---|---|---|---|---|
| Tray 54 | 259.0 | 37 647.5 | 0.00107 | 73.2 |
| Tray 55 | 239.5 | 36 210.2 | 0.00101 | 72.9 |
| Tray 56 | 220.0 | 34 773.0 | 0.00095 | 72.7 |
| Tray 57 | 206.0 | 33 895.4 | 0.00090 | 72.5 |
| Tray 58 | 192.1 | 33 017.8 | 0.00085 | 72.3 |
| Tray 59 | 178.3 | 32 140.2 | 0.00080 | 72.1 |
| Tray 60 | 166.9 | 31 526.3 | 0.00075 | 71.9 |
| Tray 61 | 155.5 | 30 912.4 | 0.00071 | 71.7 |
| Tray 62 | 144.2 | 30 298.5 | 0.00066 | 71.4 |
| Tray 63 | 126.1 | 29 725.8 | 0.00053 | 70.0 |
| Tray 64 | 108.2 | 29 153.0 | 0.00042 | 68.6 |
| Collecting tray 3 | 901.9 | 533 739.0 | 0.00019 | 68.6 |
| Tray 65 | 225.5 | 533 739.0 | 0.00005 | 68.6 |
| Tray 66 | 224.9 | 529 658.7 | 0.00004 | 65.3 |
| Tray 67 | 224.2 | 525 578.4 | 0.00003 | 61.9 |
| Tray 68 | 225.2 | 520 550.7 | 0.00002 | 56.0 |
| Tray 69 | 226.1 | 515 523.0 | 0.00001 | 50.1 |
| Tray 70 | 226.4 | 503 046.4 | 0.00001 | 48.7 |
| Tray 71 | 204.0 | 204 633.4 | 0.00003 | 47.4 |
| Tray 72 | 204.5 | 204 633.4 | 0.00002 | 44.8 |
| Tray 73 | 204.9 | 204 633.4 | 0.00002 | 42.2 |
| Tray 74 | 206.0 | 201 787.7 | 0.00001 | 37.9 |
| Tray 75 | 207.1 | 198 942.0 | 0.00001 | 33.6 |

This gives a $t_{ort}$ of only 8.79 h.

At the same time, at this $t_{ort}$ the stream containing (meth) acrylic monomers which is removed in the separating space and has the highest proportion by weight of acrylic acid is 90 987 kg/h of crude acrylic acid having an acrylic acid content of 96.9333% by weight.

An analysis shows that this improvement can be attributed, among other factors, to the liquid phase in the bottom space 5 in the example containing only 19.27% by weight of polyacrylic add (Michael adduct) as a consequence of the reduced residence time.

The invention claimed is:

1. A thermal separating process for removing at least one stream containing enriched (meth)acrylic monomers from a mixture containing (meth)acrylic monomers and components other than (meth)acrylic monomers, comprising conducting a continuous steady-state operation in at least one thermal separating apparatus which comprises a separating space with or without separating internals, into which separating space at least one stream containing (meth)acrylic monomers is conducted and out of which at least one stream containing (meth)acrylic monomers is conducted, wherein the at least one stream conducted altogether into the separating space contains, based on its total amount, X % by weight of components other than (meth)acrylic monomers, the at least one stream which is conducted out of the separating space with the highest proportion by weight of (meth)acrylic monomers contains Y % by weight of components other than (meth)acrylic monomers, the X %:Y % ratio is $\geq 5$, the separating space, except at the stream inlet and at the stream outlet points, is bounded by a solid phase and comprises at least one circulation heat exchanger, and the total volume filled with liquid phase in the separating space is $\geq 1$ m$^3$, and the temperature of at least part of the liquid phase is $\geq 80°$ C., wherein, in the case that the separating space is divided into n individual volume elements i and the highest and the lowest temperatures of the liquid phase disposed in an individual volume element i do not differ by more than 2° C. and the volume element i is continuous within the separating space, the overall residence time $t_{ort}$, $$t_{ort} = \sum_{i=1}^{n} \frac{m_{si}}{\dot{m}_i} \cdot 2^A,$$

is $\leq 20$ h, where $A = (T_i - T_o)/10°$ C., $T_o = 100°$ C., $T_i$ = the arithmetic mean of the highest and lowest temperature existing in the liquid phase of the volume element i in ° C., $m_{si}$ = the total amount of (meth)acrylic monomers present in a volume of the liquid phase present in a volume element i, $\dot{m}_i$ = the total amount of liquid phase stream conducted out of a volume element i, and $$\sum_{i=1}^{n} = \text{the sum over all volume elements } i,$$

such that the sum over all volume elements i includes neither volume elements i having a liquid phase mass $m_i$ present therein and $m_i/\dot{m}_i \geq 100$ h, as deadspace volume elements, nor volume elements i which have no liquid phase, and the total amount of the liquid phase present in the deadspace volume elements is not more than 5% by weight of the overall liquid phase present in the separating space.

2. The process as claimed in claim 1, wherein X %:Y % is $\geq 8$.

3. The process as claimed in claims 1 or 2, wherein the total volume filled with liquid phase in the separating space is $\geq 5$ m$^3$.

4. The process as claimed in claim 1, wherein the temperature of the liquid phase in the separating space is, at least partly, $\geq 100°$ C.

5. The process as claimed in claim 1, wherein the at least one (meth)acrylic monomer is selected from the group consisting of acrolein, methacrolein, acrylic acid, methacrylic acid, hydroxyethyl acrylate, hydroxyethyl methacrylate, hydroxypropyl acrylate, hydroxypropyl methacrylate, glycidyl acylate, glycidyl methacrylate, methyl acrylate, methyl methacrylate, n-butyl acrylate, isobutyl acrylate, isobutyl methacrylate, n-butyl methacrylate, tert-butyl acrylate, tert-butyl methacrylate, ethyl acrylate, ethyl methacrylate, 2-ethylhexyl acrylate, 2-ethylhexyl methacrylate, N,N-dimethylamino methacrylate and N,N-dimethylaminoethyl acrylate.

6. The process as claimed in claim 1, wherein $t_{ort}$ is $\leq 15$ h.

7. The process as claimed in claim 1, wherein $t_{ort}$ is $\leq 10$ h.

8. The process as claimed in claim 1, wherein the separating space comprises a separating column having mass transfer trays as separating internals.

9. The process as claimed in claim 8, wherein the mass transfer trays of the separating column, from bottom to top, are initially dual-flow trays, then hydraulically sealed cross-flow trays and finally valve trays.

10. The process as claimed in claim 1, wherein the at least one circulation heat exchanger is a circulation evaporator.

11. The process as claimed in claim 1, wherein the at least one circulation heat exchanger is a direct circulation evaporator.

12. The process as claimed in claim 1, wherein the thermal separating process is a fractional condensation of the product gas mixture of a heterogeneously catalyzed partial gas phase oxidation of propene and/or propane to acrylic acid.

13. The process as claimed in claim 1, wherein $t_{ort}$ is $\leqq 10$ h, the mixture comprising (meth)acrylic monomers is the product gas mixture of a heterogeneously catalyzed partial gas phase oxidation of propene and/or propane to acrylic acid and has an acrylic acid content of from 5 to 15% by weight, and the at least one stream which is conducted out of the separating space with the highest proportion by weight of (meth)acrylic monomers is crude acrylic acid having an acrylic acid content of $\geqq 95\%$ by weight.

* * * * *